United States Patent
Fleck et al.

(10) Patent No.: US 11,578,080 B2
(45) Date of Patent: Feb. 14, 2023

(54) THIENOPYRIMIDONES

(71) Applicant: Boehringer Ingelheim International GmbH, Ingelheim am Rhein (DE)

(72) Inventors: Martin Thomas Fleck, Munich (DE); Florian Paul Christian Binder, Maselheim (DE); Georg Dahmann, Biberach (DE); Joerg P. Hehn, Biberach an der Riss (DE); Annekatrin Charlotte Heimann, Biberach an der Riss (DE); Uta Friederike Lessel, Maselheim (DE); Jens Willwacher, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/463,942

(22) Filed: Sep. 1, 2021

(65) Prior Publication Data

US 2021/0395267 A1    Dec. 23, 2021

Related U.S. Application Data

(63) Continuation of application No. 17/071,092, filed on Oct. 15, 2020, now abandoned.

(30) Foreign Application Priority Data

Oct. 15, 2019  (EP) .................................... 19203173

(51) Int. Cl.
  *C07D 495/04* (2006.01)
  *C07D 495/14* (2006.01)

(52) U.S. Cl.
  CPC ......... *C07D 495/04* (2013.01); *C07D 495/14* (2013.01)

(58) Field of Classification Search
  CPC .......................... C07D 495/04; C07D 495/14
  See application file for complete search history.

(56) References Cited

FOREIGN PATENT DOCUMENTS

| WO | 2012085662 A1 | 6/2012 |
| WO | 2012172475 A1 | 12/2012 |
| WO | 2016023832 A1 | 2/2016 |
| WO | 2016133888 A1 | 8/2016 |
| WO | 2017060488 A1 | 4/2017 |

OTHER PUBLICATIONS

Borate et al., "Synthesis and evaluation of thieno[2,3-d]pyrimidin-4(3H)-ones as potential antitubercular agents", MEDCHEMCOMM, vol. 6, No. 12, Jan. 1, pp. 2209-2215, 2013.

El-Tombary et al., "Synthesi s and 1-13 Biological Evaluation of Some Novel Thieno[2,3-d] pyrimidine Derivatives as Potential Anti-inflammatory and Analgesie Agents", Medicinal Chemistry, vol. 9, No. 8, Oct. 1, 2013, pp. 1099-1112.

International Search Report for corresponding application, PCT/EP2020/078855, dated Nov. 16, 2020.

Schenkel et al., "11 Optimization of a Novel Quinazoline-Based Series of Transient Receptor Potential AI (TRPAI) Antagonists Demonstrating Potent in Vivo Activity 11", J . Med. Ch Em ., 2016, vol. 59, pp. 2794-28.

*Primary Examiner* — Rebecca L Anderson
(74) *Attorney, Agent, or Firm* — Philip I. Datlow

(57) ABSTRACT

This invention relates to thienopyrimidinones and their use as inhibitors of TRPA1 activity, pharmaceutical compositions containing the same, and methods of using the same as agents for treatment and/or prevention of fibrotic diseases, inflammatory and auto-immune diseases and CNS-related diseases.

33 Claims, No Drawings

THIENOPYRIMIDONES

FIELD OF THE INVENTION

This invention relates to thienopyrimidinones and their use as inhibitors of TRPA1 activity, pharmaceutical compositions containing the same, and methods of using the same as agents for treatment and/or prevention of fibrotic diseases, inflammatory and auto-immune diseases and CNS-related diseases.

BACKGROUND INFORMATION

Transient receptor potential channels (TRP channels) are a group of voltage-gated ion channels located mostly on the plasma membrane of numerous mammalian cell types. There are approximately 30 structurally related TRP channels sorted into groups: TRPA, TRPC, TRPM, TRPML, TRPN, TRPP and TRPV. Transient receptor potential cation channel, subfamily A, member 1 (TRPA1), also known as transient receptor potential ankyrin 1, is the only member of the TRPA gene subfamily. Structurally, TRPA channels are characterized by multiple N-terminal ankyrin repeats (~14 in the N-terminus of human TRPA1) that gives rise to the "A" for ankyrin designation (Montell, 2005).

TRPA1 is highly expressed in the plasma membrane of sensory neurons in the dorsal root and nodose ganglia that serve both skin and lung, as well as in small intestine, colon, pancreas, skeletal muscle, heart, brain, bladder and lymphocytes (https://www.proteinatlas.org/) as well as in human lung fibroblasts.

TRPA1 is best known as a sensor for environmental irritants giving rise to somatosensory modalities such as pain, cold and itch. TRPA1 is activated by a number of reactive, electrophilic stimuli (e.g. allyl isothiocyanate, reactive oxygen species), as well as non-reactive compounds (e.g. icilin), implicated in cough associated with asthma, chronic pulmonary obstructive disease (COPD), idiopathic pulmonary fibrosis (IPF) or post-viral cough or for chronic idiopathic cough as well as cough in sensitive patients. (Song and Chang, 2015; Grace and Belvisi, 2011). TRPA1 inhibitors are useful in the treatment of IPF in which cough is highly prevalent because of the link between cough and lung injury, based on studies showing cough-induced elevation of TGF-β (Xie et al., 2009; Froese et al., 2016; Tschumperlin et al., 2003; Yamamoto et al., 2002; Ahamed et al., 2008). TRPA1 antagonists inhibit calcium signaling triggered by cough triggers such as cigarette smoke extract (CSE) oxidative stress, inflammatory mediator release and downregulated antioxidant gene expression (Lin et al., 2015; Wang et al., 2019). TRPA1 antagonists are effective in studies of atopic dermatitis (Oh et al., 2013; Wilson et al., 2013), contact dermatitis (Liu et al., 2013), psoriasis-associated itch (Wilson et al., 2013) and IL-31-dependent itch (Cevikbas et al., 2014). A human TRPA1 gain-of-function has been associated with familial episodic pain syndrome (Kremeyer et al., 2010). A TRPA1 antagonist was effective in a behavioral model of migraine-related allodynia (Edelmayer et al., 2012). TRPA1 is selectively increased in trigeminal ganglia innervating injured teeth when compared to TRPA1 expression in trigeminal ganglia innervating healthy teeth (Haas et al., 2011). Several anaesthetics are known to be TRPA1 agonists, including isoflurane (Matta et al., 2008) providing rationale for TRPA1 inhibitors for the relief of post-surgical pain. TRPA1 knockout mice and wild type mice treated with a TRPA1 antagonist showed anxiolytic- and antidepressant-like phenotypes (de Moura et al., 2014). TRPA1 inhibitors are expected to have benefit in the treatment of diabetic neuropathy based on studies showing a mechanistic link of inverse regulation between AMPK and TRPA1 (Hiyama et al., 2018; Koivisto and Pertovaara, 2013; Wang et al., 2018). TRPA1 knockout mice exhibit smaller myocardial infarct sizes compared to wild type mice (Conklin et al., 2019). TRPA1 knockout and pharmacological intervention inhibited TNBS-induced colitis in mice (Engel et al., 2011). In a mouse brain ischaemia model, TRPA1 knock-out and TRPA1 antagonists reduce myelin damage (Hamilton et al., 2016). Urate crystals and joint inflammation are reduced in TRPA1 knockout mice in a monosodium urate mouse model of gout (Moilanen et al., 2015). TRPA1 deletion in rats ameliorated joint inflammation and hyperalgesia in a rat model of acute gout flares (Trevisan et al., 2014). Activation of TRPA1 elicits an inflammatory response in osteoarthritic chondrocytes (Nummenmaa et al., 2016). TRPA1 inhibition and genetic deletion reduces inflammatory mediators in osteoarthritic mouse chondrocytes and murine cartilage (Nummenmaa et al., 2016). Finally, TRPA1 knockout mice exhibited improvements in weight bearing on the osteoarthritic limb in an MIA-evoked knee swelling model (Horvath et al., 2016). TRPA1 is differentially expressed in the in the bladder epithelium rats (Du et al., 2007) and of patients with bladder outlet obstruction (Du et al., 2008). TRPA1 receptor modulation attenuates bladder overactivity in a rat model of spinal cord injury (Andrade et al., 2011) and intrathecal administration of TRPA1 antagonists attenuate cyclophosphamide-induced cystitis in rats with hyper-reflexia micturition (Chen et al., 2016).

It is therefore desirable to provide potent TRPA1 inhibitors.

TRPA1 inhibitors of various structural classes are reviewed in S. Skerratt, Progress in Medicinal Chemistry, 2017, Volume 56, 81-115 and in D. Preti, G. Saponaro, A. Szallasi, Pharm. Pat. Anal. (2015) 4 (2), 75-94.

WO2017/060488 discloses compounds that are antagonists of TRPA1, having the generalized structural formula

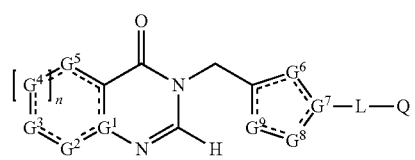

The TRPA1 activity of Examples 28 and 29 bearing a tetrazolyl ring therein is not disclosed.

L. Schenkel, et al., J. Med. Chem. 2016, 59, 2794-2809 discloses quinazolinone-based TRPA1 antagonists including compounds of the generalized structural formula

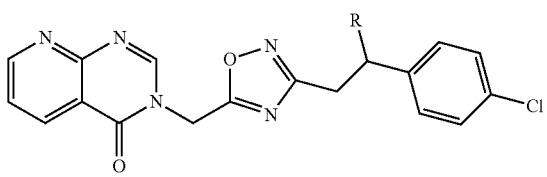

of which compound 31, wherein R is OH, is disclosed as having an antagonistic TRPA1 activity of $IC_{50}$ 58 nM in a FLIPR assay and having an intrinsic clearance in human liver microsomes of <14 µL/min/kg.

DETAILED DESCRIPTION OF THE INVENTION

The present invention provides novel thienopyrimidinones that are surprisingly potent inhibitors of TRPA1 (Assay A), further characterised by improved stability in human liver microsomes (Assay B)

improved stability in human hepatocytes (Assay C).

Compounds of the present invention differ structurally from examples 28 and 29 in WO2017/060488 in that they contain a thienopyrimidinone core with amido substituents as well as substituents adjacent to a secondary aliphatic alcohol. Compounds of the present invention additionally differ structurally from example 31 in L. Schenkel, et al., J. Med. Chem. 2016, 59, 2794-2809, in that they bear a tetrazolyl ring. These structural differences unexpectedly lead to a favourable combination of (i) inhibition of TRPA1, (ii) stability in human liver microsomes, (iii) stability in human hepatocytes, and (iv) fewer unwanted human metabolites.

Compounds of the invention are thus superior to those disclosed in the prior art in terms of the combination of the following parameters:

potency as inhibitors of TRPA1 stability in human liver microsomes stability in human hepatocytes giving rise to fewer unwanted human metabolites Stability in human liver microsomes refers to the susceptibility of compounds to biotransformation in the context of selecting and/or designing drugs with favorable pharmacokinetic properties as a first screening step. The primary site of metabolism for many drugs is the liver. Human liver microsomes contain the cytochrome P450s (CYPs), and thus represent a model system for studying phase I drug metabolism in vitro. Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs. Therefore, compounds of the present invention in addition to being able to inhibit TRPA1 are expected to have a favorable in vivo clearance and thus the desired duration of action in humans.

Stability in human hepatocytes refers to the susceptibility of compounds to biotransformation in the context of selecting and/or designing drugs with favorable pharmacokinetic properties. The primary site of metabolism for many drugs is the liver. Human hepatocytes contain the cytochrome P450s (CYPs) and other drug metabolizing enzymes, and thus represent a model system for studying drug metabolism in vitro. (Importantly, in contrast to liver microsomes assay, the hepatocytes assay covers also phase II biotransformations as well as liver-specific transporter-mediated processes, and therefore represents a more complete system for drug metabolism studies). Enhanced stability in human hepatocytes is associated with several advantages, including increased bioavailability and adequate half-life, which can enable lower and less frequent dosing of patients. Thus, enhanced stability in human hepatocytes is a favorable characteristic for compounds that are to be used for drugs.

The present invention provides novel compounds according to formula (I)

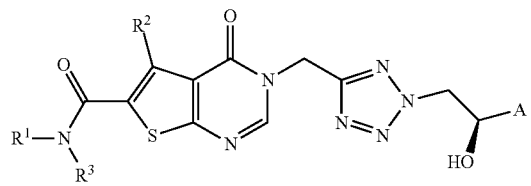

wherein

A is selected from the group consisting of phenyl, naphthyl, thiophenyl, benzothiophenyl or benzofuranyl, optionally substituted with one or two members of the group consisting of H, F, Cl, Br, $C_{1-4}$-alkyl, $F_{1-3}$-fluoro-$C_{1-4}$-alkyl, CN, $OCH_3$, cyclopropyl, and cyclobutyl, or A is selected from

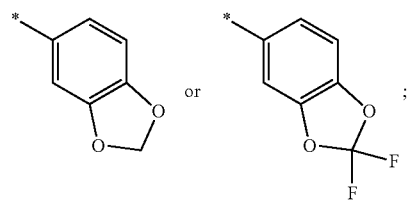 [SMILES: *c1ccc2c(c1)OCO2 ; *c1ccc2c(c1)OC(F)(F)O2]

and $R^1$ is selected from H, $C_{1-4}$-alkyl, $F_{1-3}$-fluoro-$C_{1-4}$-alkyl, $C_{1-4}$-alkyl-OH or $C_{1-4}$-alkyl-CN;

$R^2$ is selected from $C_{1-2}$-alkyl or Cl;

or $R^1$ and $R^2$ are each $CH_2$ joined via a bond forming a 6-membered ring;

$R^3$ is selected from H, or $C_{1-4}$-alkyl.

Another embodiment of the present invention relates to a compound of formula (I), wherein A is selected from the group consisting of phenyl, thiophenyl or benzofuranyl, optionally substituted with one or two members of the group consisting of H, F, Cl, Br, $C_{1-4}$-alkyl, $F_{1-3}$-fluoro-$C_{1-4}$-alkyl, CN, $OCH_3$, cyclopropyl, and cyclobutyl, or A is selected from

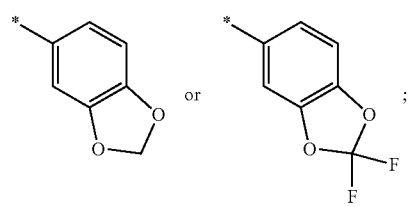 [SMILES: *c1ccc2c(c1)OCO2 ; *c1ccc2c(c1)OC(F)(F)O2]

and substituents $R^1$ and $R^2$ are defined as in any of the preceding embodiments.

Another embodiment of the present invention relates to a compound of formula (I), wherein A is selected from the group consisting of phenyl, thiophenyl or benzofuranyl, optionally substituted with one or two members of the group consisting of H, F, Cl, Br, $C_{1-4}$-alkyl, $F_{1-3}$-fluoro-$C_{1-4}$-alkyl, CN, $OCH_3$, cyclopropyl, and cyclobutyl, or
A is selected from

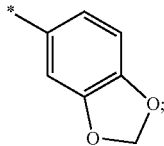 [SMILES: *c1ccc2c(c1)OCO2]

and substituents R¹ and R² are defined as in any of the preceding embodiments.

Another embodiment of the present invention relates to a compound of formula (I), wherein A is selected from the group consisting of phenyl, thiophenyl or benzofuranyl, optionally substituted with one or two members of the group consisting of H, F, Br, Cl, and $CH_3$;
or
A is selected from

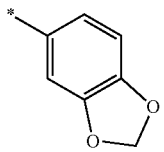 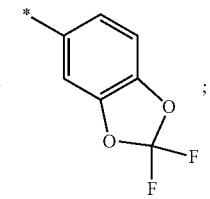

and substituents R¹ and R² are defined as in any of the preceding embodiments.

Another embodiment of the present invention relates to a compound of formula (I), wherein A is selected from the group consisting of phenyl, thiophenyl or benzofuranyl, optionally substituted with one or two members of the group consisting of H, F, Br, Cl, and —$CH_3$;
or
A is selected from

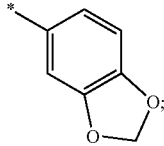 [SMILES: *c1ccc2c(c1)OCO2]

and substituents R¹ and R² are defined as in any of the preceding embodiments.

Another embodiment of the present invention relates to a compound of formula (I), wherein A is selected from the group consisting of

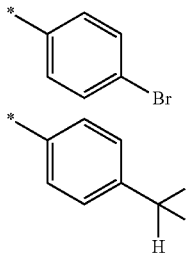 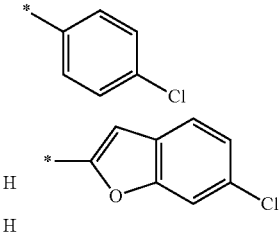

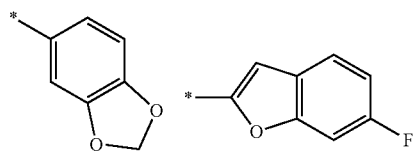
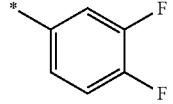
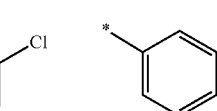
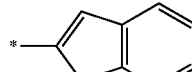

and substituents R¹ and R² are defined as in any of the preceding embodiments. Another embodiment of the present invention relates to a compound of formula (I), wherein R¹ is selected from the group consisting of H and $C_{1-4}$-alkyl; and substituents A and R² are defined as in any of the preceding embodiments.

Another embodiment of the present invention relates to a compound of formula (I), wherein R¹ is selected from the group consisting of H and $H_3C$; and substituents A and R² are defined as in any of the preceding embodiments.

Another embodiment of the present invention relates to a compound of formula (I), wherein R² is $H_3C$ or Cl; and substituents A and R¹ are defined as in any of the preceding embodiments.

Another embodiment of the present invention relates to a compound of formula (I), wherein R³ is H or $H_3C$; and substituents A, R¹ and R² are defined as in any of the preceding embodiments.

Preferred is a compound of formula (I), selected from the group consisting of

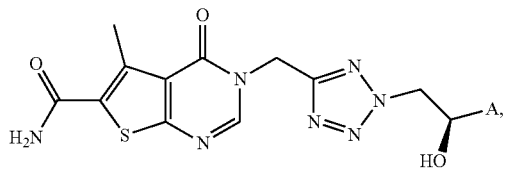

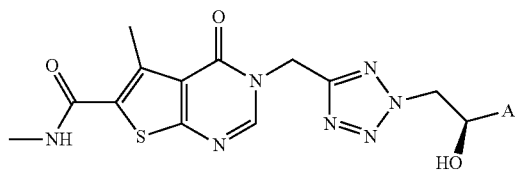

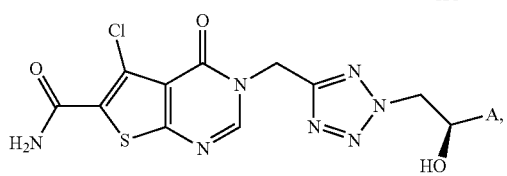

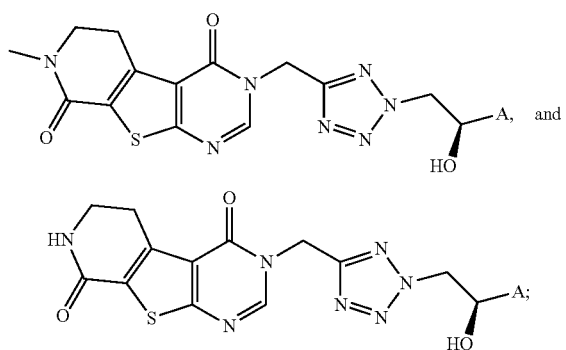
and substituent A is defined as in any of the preceding embodiments.
Particularly preferred is the compound according to formula (I) selected from the group consisting of
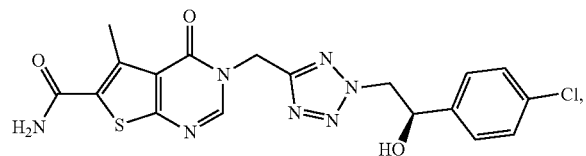
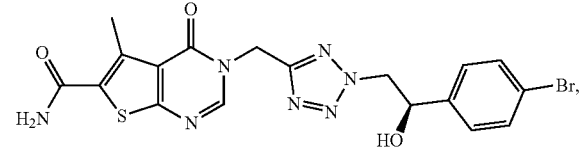
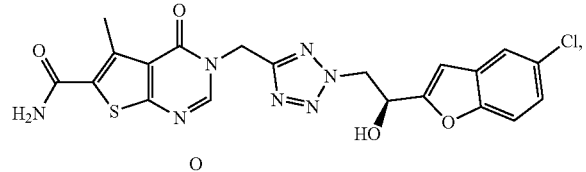
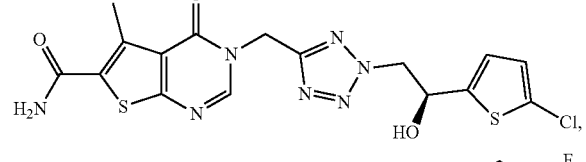
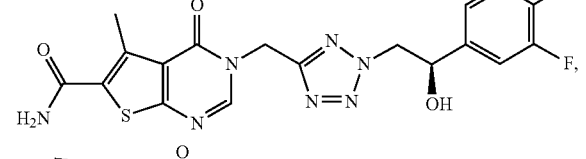
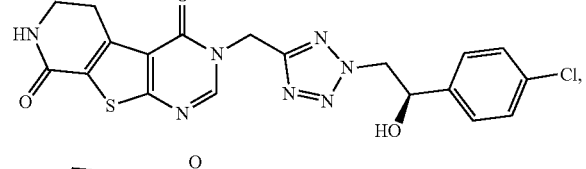
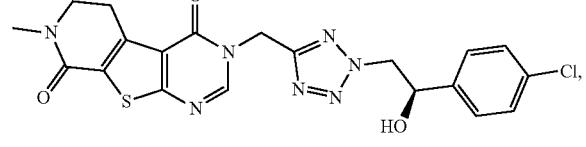
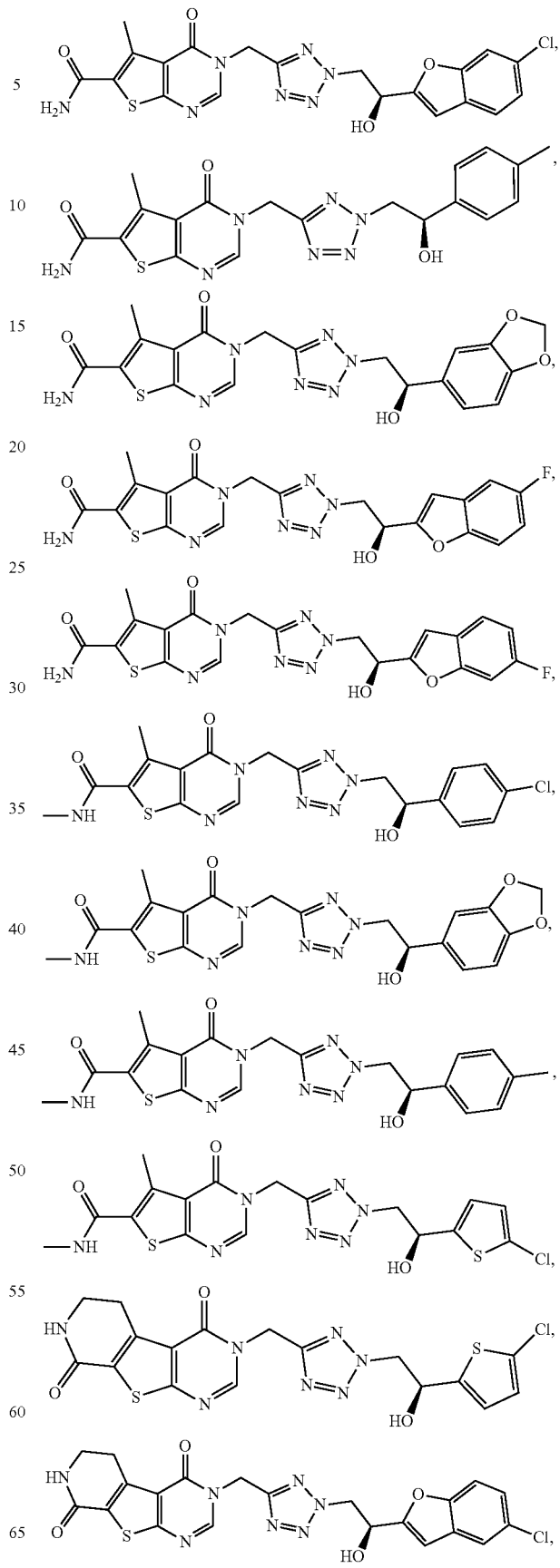

-continued

[chemical structures]

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

The numeration of the atoms of a substituent starts with the atom that is closest to the core or to the group to which the substituent is attached.

For example, the term "3-carboxypropyl-group" represents the following substituent:

[structure]

wherein the carboxy group is attached to the third carbon atom of the propyl group. The terms "1-methylpropyl-", "2,2-dimethylpropyl-" or "cyclopropylmethyl-" group represent the following groups:

[structures]

The asterisk may be used in sub-formulas to indicate the bond that is connected to the core molecule as defined.

The term "$C_{1-n}$-alkyl", wherein n is an integer selected from 2, 3, 4 or 5, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$F_{1-m}$-fluoro-$C_{1-n}$-alkyl", wherein m is an integer selected from 2 or 3, and n is an integer selected from 2, 3, 4 or 5, denotes an $C_{1-n}$-alkyl group as defined hereinbefore wherein one or more hydrogen atoms are replaced by 1-m fluorine. For example, $F_{1-3}$-fluoro-$C_{1-2}$-alkyl embraces the radicals $FH_2C$, $F_2HC$, $F_3C$, $FH_2C$—$H_2C$, $F_2HC$—$H_2C$, $F_3C$—$H_2C$, $FH_2C$—$FHC$, $FH_2C$—$F_2C$, $F_2HC$—$FHC$, $H_3C$—$FHC$, and $H_3C$—$F_2C$.

The term phenyl refers to the radical of the following ring

[structure]

The term naphthyl refers to the radical of the following ring

[structure]

The term thiophenyl refers to the radical of the following ring

[structure]

The term thienopyrimidone refers to the radical of the following ring

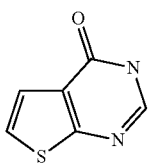

and includes

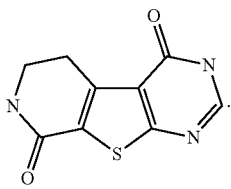 [SMILES: O=C1NCCc2c1sc1nc[nH]c(=O)c21]

The term benzothiophenyl refers to the radical of the following ring

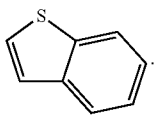

The term benzofuranyl refers to the radical of the following ring

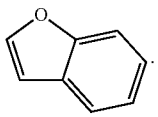

The term cyclopropyl refers to the radical of the following ring

The term cyclobutyl refers to the radical of the following ring

The term tetrazolyl refers to the radical of the following ring

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound forms a salt or a complex with an acid or a base. Examples of acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane. The pharmaceutically acceptable salts of the present invention can be synthesized from the parent compound that contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts,) also comprise a part of the present invention.

Biological Assays

Assay A: TRPA1 Assay

The activity of the compounds of the invention may be demonstrated using the following in vitro TRPA1 cell assay:

Method:

A human HEK293 cell line over-expressing the human TRPA1 ion channel (Perkin Elmer, Product No. AX-004-PCL) was used as a test system for compound efficacy and potency. Compound activity was determined by measuring the effect of compounds on intracellular calcium concentration induced by AITC (Allylisothiocyanat) agonism in a FLIPRtetra system (Molecular Devices).

Cell culture:

The cells were obtained as frozen cells in cryo-vials and stored until use at −150° C. Cells were grown in culture medium (MEM/EBSS medium with 10% FCS and 0.4 mg/ML Geneticin). It is important that density does not exceed 90% confluence. For sub-culturing cells were detached from flasks by Versene. At the day before the assay, cells were detached, washed twice with medium (MEM/EBSS medium with 10% FCS) and 20000 cells in 20 µl/well were seeded to Poly D-Lysin biocoated 384-well plates (black, clear bottom, Cat. 356697) from Corning. Plates were incubated for 24 hours at 37° C./5% CO2 before use in the assay.

Compound Preparation

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared, further intermediate dilutions (1:20) of the substances were carried out with HBSS/HEPES buffer (1×HEPES, Cat. 14065 from Gibco, 20 mM HEPES, Cat. 83264 from SIGMA, 0.1% BSA Cat. 11926 from Invitrogen, pH 7,4

Flipr Assay:

At the assay day cells were washed 3× with assay puffer, 20 µL buffer remained in the wells after washing. 10 µL Ca6 kit (Cat. R8191 MolecularDevices) loading buffer in HBSS/HEPES was added to the cells and the plates were incubated with lid for 120 minutes at 3775% CO2. 10 µL of compound or controls in HBSS/HEPES buffer/5% DMSO from the intermediate dilution plate were carefully added to the wells. Luminescence (indicating the calcium influx or release) was read on the FLIPRtetra device for 10 minutes to monitor the compound induced effects (e.g. agonism). Finally 10 µL of the agonist AITC 50 µM dissolved in HBSS/HEPES buffer/ 0.05% DMSO (final concentration 10 µM) was added to the wells followed by an additional read on the FLIPRtetra device for 10 minutes. The area under the signal curve (AUC) after AITC addition was used for IC50/% inhibition calculations Data Evaluation and Calculation:

Each assay microtiter plate contained wells with vehicle (1% DMSO) controls instead of compound as controls for AITC induced luminescence (100% CTL; high controls) and wells with vehicle controls without AITC as controls for non-specific changes in luminescence (0% CTL; low controls).

The analysis of the data was performed by the calculation of the area under signal curve of the individual wells. Based on this values the % value for the measurement of each substance concentration was calculated (AUC(sample)−AUC(low))*100/(AUC(high)−AUC(low)) using MegaLab software (in house development). The IC50 values were calculated from the % control values using MegaLab software. Calculation: $[y=(a-d)/(1+(x/c)^b)+d]$, a=low value, d=high value; x=cone M; c=IC50 M; b=hill; y=% ctrl

TABLE 1

Biological data for compounds of the invention as obtained in Assay A

| Example | hTRPA1 $IC_{50}$ [nM] |
|---|---|
| 1 | 11 |
| 2 | 12 |
| 3 | 12 |
| 4 | 12 |
| 5 | 74 |
| 6 | 11 |
| 7 | 16 |
| 8 | 15 |
| 9 | 21 |
| 10 | 28 |
| 11 | 25 |
| 12 | 17 |
| 13 | 20 |
| 14 | 76 |
| 15 | 38 |
| 16 | 37 |
| 17 | 14 |
| 18 | 14 |
| 19 | 31 |
| 20 | 14 |
| 21 | 80 |
| 22 | 7 |
| 23 | 6 |

TABLE 2

Biological data for prior art compounds (examples 28 and 29 in WO2017/060488) as obtained in Assay A.

| Example in WO2017/060488 | hTRPA1 $IC_{50}$ [nM] |
|---|---|
| 28 | 366 |
| 29 | 1120 |

TABLE 3

Biological data for prior art compounds (example 31 in L. Schenkel, et al., J. Med. Chem. 2016, 59, 2794-2809) as obtained in Assay A.

| Example in Med. Chem. 2016, 59, 2794-2809 | hTRPA1 $IC_{50}$ [nM] |
|---|---|
| 31 | 52 |

Assay B: Microsomal Clearance:

The metabolic degradation of the test compound is assayed at 37° C. with pooled liver microsomes. The final incubation volume of 100 µl per time point contains TRIS buffer pH 7.6 at RT (0.1 M), magnesium chloride (5 mM), microsomal protein (1 mg/ml) and the test compound at a final concentration of 1 µM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points (0, 5, 15, 30, 60 min). Additionally, the NADPH-independent degradation is monitored in incubations without NADPH, terminated at the last time point. The [%] remaining test compound after NADPH independent incubation is reflected by the parameter c(control) (metabolic stability). The quenched incubations are pelleted by centrifugation (10000 g, 5 min).

An aliquot of the supernatant is assayed by LC-MS/MS for the amount of parent compound. The half-life (t½ INVITRO) is determined by the slope of the semilogarithmic plot of the concentration-time profile.

The intrinsic clearance (CL_INTRINSIC) is calculated by considering the amount of protein in the incubation:

CL_INTRINSIC [µl/min/mg protein]=(Ln 2/(half-life [min]*protein content [mg/ml]))*1000

CL_INTRINSIC_INVIVO [ml/min/kg]=(CL_INTRINSIC [µL/min/mg protein]×MPPGL [mg protein/g liver]×liver factor [g/kg body weight])/1000

Qh [%]=CL [ml/min/kg]/hepatic blood flow [ml/min/kg])

Hepatocellularity, human: 120×10e6 cells/g liver

Liver factor, human: 25.7 g/kg bodyweight

Blood flow, human: 21 ml/(min×kg)

TABLE 4

Biological data for compounds of the invention as obtained in Assay B

| Example | human LM [% Qh] |
|---|---|
| 1 | <23 |
| 2 | <23 |
| 3 | <23 |
| 4 | <23 |
| 5 | <23 |
| 6 | <23 |
| 7 | 36 |
| 8 | 43 |
| 9 | <23 |
| 10 | <23 |
| 11 | <23 |
| 12 | <23 |
| 13 | <23 |
| 14 | <23 |
| 15 | <23 |
| 16 | <23 |
| 17 | <23 |
| 18 | 32 |
| 19 | <23 |
| 20 | <23 |
| 21 | 27 |
| 22 | 35 |
| 23 | <23 |

TABLE 5

Biological data for prior art compounds (examples 28 and 29 in WO2017/060488) as obtained in Assay B.

| Example in WO2017/060488 | human LM [% Qh] |
|---|---|
| 28 | 62 |
| 29 | <23 |

TABLE 6

Biological data for prior art compounds (example 31 in L. Schenkel, et al., J. Med. Chem. 2016, 59, 2794-2809) as obtained in Assay B.

| Example in Med. Chem. 2016, 59, 2794-2809 | human LM [% Qh] |
|---|---|
| 31 | <23 |

Assay C: Hepatocyte Clearance

The metabolic degradation of the test compound is assayed in a hepatocyte suspension. Hepatocytes (cryopreserved) are incubated in. Dulbecco's modified eagle medium (supplemented with 3.5 µg glucagon/500 mL, 2.5 mg insulin/500 mL and 3.75 mg/500 mL hydrocortison) containing 5% or 50% species serum.

Following a 30 min preincubation in an incubator (37° C., 10% $CO_2$) 5 µl of test compound solution (80 µM; from 2 mM in DMSO stock solution diluted 1:25 with medium) are added into 395 µl hepatocyte suspension (cell density in the range 0.25-5 Mio cells/mL depending on the species, typically 1 Mio cells/mL; final concentration of test compound 1 µM, final DMSO concentration 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS

CLint is calculated as follows CL_INTRINSIC=Dose/AUC=(C0/CD)/(AUD+clast/k)×1000/60. CO: initial concentration in the incubation [µM], CD: cell density of vital cells [10e6 cells/mL], AUD: area under the data [µM×h], clast: concentration of last data point [µM], k: slope of the regression line for parent decline [h-1].

The calculated in vitro hepatic intrinsic clearance can be scaled up to the intrinsic in vivo hepatic Clearance and used to predict hepatic in vivo blood clearance (CL) by the use of a liver model (well stirred model).

CL_INTRINSIC_INVIVO [ml/min/kg]=(CL_INTRINSIC [µL/min/10e6 cells]×hepatocellularity [10e6 cells/g liver]×liver factor [g/kg body weight])/1000

CL [ml/min/kg]=CL_INTRINSIC_INVIVO [ml/min/kg]×hepatic blood flow [ml/min/kg]/(CL_INTRINSIC_INVIVO [ml/min/kg]+hepatic blood flow [ml/min/kg])

Qh [%]=CL [ml/min/kg]/hepatic blood flow [ml/min/kg])

Hepatocellularity, human: 120×10e6 cells/g liver
Liver factor, human: 25.7 g/kg bodyweight
Blood flow, human: 21 ml/(min×kg)

TABLE 7

Biological data for compounds of the invention as obtained in Assay C

| Example | human Hepatocytes [% Qh] |
|---|---|
| 1 | 12 |
| 2 | 13 |
| 3 | 40 |
| 4 | 7 |
| 5 | n.d. |
| 6 | 7 |
| 7 | 26 |
| 8 | 36 |
| 9 | 16 |
| 10 | 14 |
| 11 | 28 |
| 12 | 31 |
| 13 | 9 |
| 14 | 13 |
| 15 | 18 |
| 16 | 17 |
| 17 | 22 |
| 18 | 48 |
| 19 | 26 |
| 20 | 28 |
| 21 | 5 |
| 22 | 44 |
| 23 | 12 |

TABLE 8

Biological data for prior art compounds (examples 28 and 29 in WO2017/060488) as obtained in Assay C.

| Example in WO2017/060488 | human Hepatocytes [% Qh] |
|---|---|
| 28 | 49 |
| 29 | 22 |

TABLE 9

Biological data for prior art compounds (example 31 in L. Schenkel, et al., J. Med. Chem. 2016, 59, 2794-2809) as obtained in Assay C.

| Example in Med. Chem. 2016, 59, 2794-2809 | human Hepatocytes [% Qh] |
|---|---|
| 31 | 73 |

Assay D: Metabolism in Human Hepatocytes In Vitro

The metabolic pathway of a test compound is investigated using primary human hepatocytes in suspension. After recovery from cryopreservation, human hepatocytes are incubated in Dulbecco's modified eagle medium containing 5% human serum and supplemented with 3.5 µg glucagon/500 ml, 2.5 mg insulin/500 ml and 3.75 mg/500 ml hydrocortisone.

Following a 30 min preincubation in a cell culture incubator (37° C., 10% $CO_2$), test compound solution is spiked into the hepatocyte suspension to obtain a final cell density of $1.0*10^6$ to $4.0*10^6$ cells/ml (depending on the metabolic turnover rate of the compound observed with primary human hepatocytes), a final test compound concentration of 10 µM, and a final DMSO concentration of 0.05%.

The cells are incubated for six hours in a cell culture incubator on a horizontal shaker, and samples are removed from the incubation after 0, 0.5, 1, 2, 4 or 6 hours, depending on the metabolic turnover rate. Samples are quenched with acetonitrile and pelleted by centrifugation. The supernatant is transferred to a 96-deepwell plate, evaporated under nitrogen and resuspended prior to bioanalysis by liquid chromatography-high resolution mass spectrometry for identification of putative metabolites.

TABLE 10

Major metabolites observed for Example 6 of the invention as obtained by Assay D:

| Cpd | Metabolite M1 | Mechanism |
|---|---|---|
| Metabolite M1 | 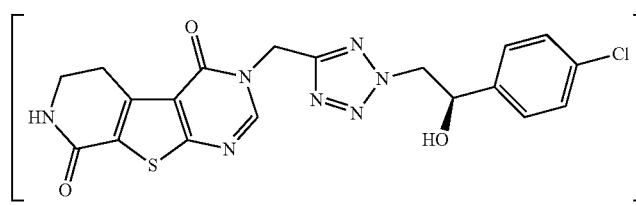 +o | Oxygenation |
| Metabolite M2 | 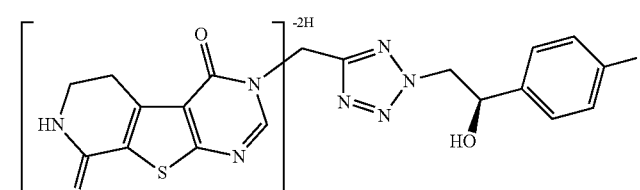 -2H | Dehydrogenation |

TABLE 10-continued

Major metabolites observed for Example 6 of the invention as obtained by Assay D:

| Cpd | Metabolite M1 | | Mechanism |
|---|---|---|---|
| Metabolite M3 | [structure] | +Gluc | Glucuronidation |

The integrity of tetrazole ring was not affected in any of the major described metabolites, based on tentative LC-MS" structure elucidation.

Method of Treatment

The present invention is directed to compounds of general formula 1 which are useful in the prevention and/or treatment of a disease and/or condition associated with or modulated by TRPA1 activity, including but not limited to the treatment and/or prevention of fibrotic disease, inflammatory and immunoregulatory disorders, respiratory or gastrointestinal diseases or complaints, ophthalmic diseases, inflammatory diseases of the joints and inflammatory diseases of the nasopharynx, eyes, and skin. Said disorders, diseases and complaints include cough, idiopathic pulmonary fibrosis, other pulmonary interstitial diseases and other fibrotic, asthma or allergic diseases, eosinophilic diseases, chronic obstructive pulmonary disease, as well as autoimmune pathologies, such as rheumatoid arthritis and atherosclerosis, pain and neurological disorders, such as depression.

The compounds of general formula 1 are useful for the prevention and/or treatment of:

(1) Cough such as chronic idiopathic cough or chronic refractory cough, cough associated with asthma, COPD and lung cancer and post-viral cough.

(2) Pulmonary fibrotic diseases such as pneumonitis or interstitial pneumonitis associated with collagenosis, e.g. lupus erythematodes, systemic scleroderma, rheumatoid arthritis, polymyositis and dermatomysitis, idiopathic interstitial pneumonias, such as pulmonary lung fibrosis (IPF), non-specific interstitial pneumonia, respiratory bronchiolitis associated interstitial lung disease, desquamative interstitial pneumonia, cryptogenic orgainizing pneumonia, acute interstitial pneumonia and lymphocytic interstitial pneumonia, lymangioleiomyomatosis, pulmonary alveolar proteinosis, Langerhan's cell histiocytosis, pleural parenchymal fibroelastosis, interstitial lung diseases of known cause, such as interstitial pneumonitis as a result of occupational exposures such as asbestosis, silicosis, miners lung (coal dust), farmers lung (hay and mould), Pidgeon fanciers lung (birds) or other occupational airbourne triggers such as metal dust or mycobacteria, or as a result of treatment such as radiation, methotrexate, amiodarone, nitrofurantoin or chemotherapeutics, or for granulomatous disease, such as granulomatosis with polyangitis, Churg-Strauss syndrome, sarcoidosis, hypersensitivity pneumonitis, or interstitial pneumonitis caused by different origins, e.g. aspiration, inhalation of toxic gases, vapors, bronchitis or pneumonitis or interstitial pneumonitis caused by heart failure, X-rays, radiation, chemotherapy, M. boeck or sarcoidosis, granulomatosis, cystic fibrosis or mucoviscidosis, or alpha-1-antitrypsin deficiency.

(3) Other fibrotic diseases such as hepatic bridging fibrosis, liver cirrhosis, non-alcoholic steatohepatitis (NASH), atrial fibrosis, endomyocardial fibrosis, old myocardial infarction, glial scar, arterial stiffness, arthrofibrosis, Dupuytren's contracture, keloid, scleroderma/systemic sclerosis, mediastinal fibrosis, myelofibrosis, Peyronie's disease, nephrogenic systemic fibrosis, retroperitoneal fibrosis, adhesive capsulitis.

(4) Inflammatory, auto-immune or allergic diseases and conditions such as allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, hyperreactive airways, allergic conjunctivitis, bronchiectasis, adult respiratory distress syndrome, bronchial and pulmonary edema, bronchitis or pneumonitis, eosinophilic cellulites (e.g., Well's syndrome), eosinophilic pneumonias (e.g., Loeffler's syndrome, chronic eosinophilic pneumonia), eosinophilic fasciitis (e. g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophiliamyalgia syndrome due to the ingestion of contaminated tryptophane, insect sting allergies; autoimmune diseases, such as rheumatoid arthritis, Graves' disease, Sjogren's syndrome psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); erythema nodosum; eosinophilic myositis, eosinophilic fasciitis, cancers with leukocyte infiltration of the skin or organs; ophthalmic diseases such as age related macular degeneration, diabetic retinopathy and diabetic macular edema, keratitis, eosinophilic keratitis, keratoconjunctivitis, vernal keratoconjunctivitis, scarring, anterior segment scarring, blepharitis, blepharoconjunctivitis, bullous disorders, cicatricial pemphigoid, conjunctival melanoma, papillary conjunctivitis, dry eye, episcleritis, glaucoma, gliosis, Granuloma annulare, Graves' ophthalmopathy, intraocular melanoma, Pinguecula, proliferative vitreoretinopathy, pterygia, scleritis, uveitis, acute gout flares, gout or osteoarthritis.

(5) Pain such as chronic idiopathic pain syndrome, neuropathic pain, dysesthesia, allodynia, migraine, dental pain and post-surgical pain.

(6) Depression, anxiousness, diabetic neuropathy and bladder disorders such as bladder outlet obstruction, overactive bladder, cystitis; myocardial reperfusion injury or brain ischaemia injury.

Accordingly, the present invention relates to a compound of general formula 1 for use as a medicament.

Furthermore, the present invention relates to the use of a compound of general formula 1 for the treatment and/or prevention of a disease and/or condition associated with or modulated by TRPA1 activity.

Furthermore, the present invention relates to the use of a compound of general formula 1 for the treatment and/or prevention of fibrotic disease, inflammatory and immunoregulatory disorders, respiratory or gastrointestinal diseases or complaints, ophthalmic diseases, inflammatory diseases of the joints and inflammatory diseases of the nasopharynx, eyes, and skin. Said disorders, diseases and complaints include cough, idiopathic pulmonary fibrosis, other pulmonary interstitial diseases and other fibrotic, asthma or allergic diseases, eosinophilic diseases, chronic obstructive pulmonary disease, as well as autoimmune pathologies, such as rheumatoid arthritis and atherosclerosis.

Furthermore, the present invention relates to the use of a compound of general formula 1 for the treatment and/or prevention of:

(1) Cough such as chronic idiopathic cough or chronic refractory cough, cough associated with asthma, COPD and lung cancer and post-viral cough.

(2) Pulmonary fibrotic diseases such as pneumonitis or interstitial pneumonitis associated with collagenosis, e.g. lupus erythematodes, systemic scleroderma, rheumatoid arthritis, polymyositis and dermatomysitis, idiopathic interstitial pneumonias, such as pulmonary lung fibrosis (IPF), non-specific interstitial pneumonia, respiratory bronchiolitis associated interstitial lung disease, desquamative interstitial pneumonia, cryptogenic orgainizing pneumonia, acute interstitial pneumonia and lymphocytic interstitial pneumonia, lymangioleiomyomatosis, pulmonary alveolar proteinosis, Langerhan's cell histiocytosis, pleural parenchymal fibroelastosis, interstitial lung diseases of known cause, such as interstitial pneumonitis as a result of occupational exposures such as asbestosis, silicosis, miners lung (coal dust), farmers lung (hay and mould), Pidgeon fanciers lung (birds) or other occupational airbourne triggers such as metal dust or mycobacteria, or as a result of treatment such as radiation, methotrexate, amiodarone, nitrofurantoin or chemotherapeutics, or for granulomatous disease, such as granulomatosis with polyangitis, Churg-Strauss syndrome, sarcoidosis, hypersensitivity pneumonitis, or interstitial pneumonitis caused by different origins, e.g. aspiration, inhalation of toxic gases, vapors, bronchitis or pneumonitis or interstitial pneumonitis caused by heart failure, X-rays, radiation, chemotherapy, M. boeck or sarcoidosis, granulomatosis, cystic fibrosis or mucoviscidosis, or alpha-1-antitrypsin deficiency.

(3) Other fibrotic diseases such as heaptic bridging fibrosis, liver cirrhosis, non-alcoholic steatohepatitis (NASH), atrial fibrosis, endomyocardial fibrosis, old myocardial infarction, glial scar, arterial stiffness, arthrofibrosis, Dupuytren's contracture, keloid, scleroderma/systemic sclerosis, mediastinal fibrosis, myelofibrosis, Peyronie's disease, nephrogenic systemic fibrosis, retroperitoneal fibrosis, adhesive capsulitis.

(4) Inflammatory, auto-immune or allergic diseases and conditions such as allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, hyperreactive airways, allergic conjunctivitis, bronchiectasis, adult respiratory distress syndrome, bronchial and pulmonary edema, bronchitis or pneumonitis, eosinophilic cellulites (e.g., Well's syndrome), eosinophilic pneumonias (e.g., Loeffler's syndrome, chronic eosinophilic pneumonia), eosinophilic fasciitis (e. g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophiliamyalgia syndrome due to the ingestion of contaminated tryptophane, insect sting allergies; autoimmune diseases, such as rheumatoid arthritis, Graves' disease, Sjogren's syndrome psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); erythema nodosum; eosinophilic myositis, eosinophilic fasciitis, cancers with leukocyte infiltration of the skin or organs; ophthalmic diseases such as age related macular degeneration, diabetic retinopathy and diabetic macular edema, keratitis, eosinophilic keratitis, keratoconjunctivitis, vernal keratoconjunctivitis, scarring, anterior segment scarring, blepharitis, blepharoconjunctivitis, bullous disorders, cicatricial pemphigoid, conjunctival melanoma, papillary conjunctivitis, dry eye, episcleritis, glaucoma, gliosis, Granuloma annulare, Graves' ophthalmopathy, intraocular melanoma, Pinguecula, proliferative vitreoretinopathy, pterygia, scleritis, uveitis, acute gout flares, gout or osteoarthritis.

(5) Pain such as chronic idiopathic pain syndrome, neuropathic pain, dysesthesia, allodynia, migraine, dental pain and post-surgical pain.

(6) Depression, anxiousness, diabetic neuropathy and bladder disorders such as bladder outlet obstruction, overactive bladder, cystitis; myocardial reperfusion injury or brain ischaemia injury.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect of the present invention the present invention relates to methods for the treatment or prevention of above mentioned diseases and conditions, which method comprises the administration of an effective amount of a compound of general formula 1 to a human being.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with fibrotic diseases, inflammatory and immunoregulatory disorders, respiratory or gastrointestinal diseases or complaints, inflammatory diseases of the joints or of the nasopharynx, eyes, and skin or conditions such as for example cough, idiopathic pulmonary fibrosis, other pulmonary interstitial diseases, asthma or allergic diseases, eosinophilic diseases, chronic obstructive pulmonary disease, atopic dermatitis as well as autoimmune pathologies, such as rheumatoid arthritis and atherosclerosis, or therapeutic agents useful for the treatment of ophthalmic diseases, pain and depression.

Additional therapeutic agents that are suitable for such combinations include in particular those, which, for example, potentiate the therapeutic effect of one or more active substances with respect to one of the indications mentioned and/or allow the dosage of one or more active substances to be reduced.

Therefore, a compound of the invention may be combined with one or more additional therapeutic agents selected from the group consisting of antifibrotic agents, anti-tussive agents, anti-inflammatory agents, anti-atopic dermatitis agents, analgesics, anti-convulsants, anxiolytics, sedatives, skeletal muscle relaxants or anti-depressants.

Antifibrotic agents are for example nintedanib, pirfenidone, phosphodiesterase-IV (PDE4) inhibitors such as roflumilast, autotaxin inhibitors such as GLPG-1690 or BBT-877; connective tissue growth factor (CTGF) blocking antibodies such as Pamrevlumab; B-cell activating factor receptor (BAFF-R) blocking antibodies such as Fanalumab; alpha-V/beta-6 blocking inhibitors such as BG-00011/STX-100, recombinant pentraxin-2 (PTX-2) such as PRM-151; c-Jun N-terminal kinase (JNK) inhibitors such as CC-90001; galectin-3 inhibitors such as TD-139; G-protein coupled receptor 84 (GPR84) inhibitors such as GLPG1205; G-protein coupled receptor 84/G-protein coupled receptor 40 dual inhibitors such as PB1-4050; Rho Associated Coiled-Coil Containing Protein Kinase 2 (ROCK2) inhibitors such as KD-025; heat shock protein 47 (HSP47) small interfering RNA such as BMS986263/ND-F02-s0201; Wnt pathway inhibitor such as SM-04646; FD4/PDE3/4 inhibitors such as Tipelukast; recombinant immuno-modulatory domains of histidyl tRNA synthetase (HARS) such as ATYR-1923; prostaglandin synthase inhibitors such as ZF-2102/SAR-191801; 15-hydroxy-eicosapentaenoic acid (15-HEPE e.g. DS-102); Lysyl Oxidase Like 2 (LOXL2) inhibitors such as PAT-1251, PXS-5382/PXS-5338; phosphoinositide 3-kinases (PI3K)/mammalian target of rapamycin (mTOR) dual inhibitors such as HEC-68498; calpain inhibitors such as BLD-2660; mitogen-activated protein kinase kinase kinase (MAP3K19) inhibitors such as MG-S-2525; chitinase inhibitors such as OATD-01; mitogen-activated protein kinase-activated protein kinase 2 (MAPKAPK2) inhibitors such as MMI-0100; transforming growth factor beta 1 (TGF-beta1) small interfering RNA such as TRK250/BNC-1021; or lysophosphatidic acid receptor antagonists such as BMS986278.

Anti-tussive agents are, for example, purinoceptor 3 (P2X3) receptor antagonists such as gefapixant, S-600918, BAY-1817080, or BLU-5937; neurokinin 1 (NK-1) receptor antagonist such as Orvepitant, Aprepitant; nicotinic acetylcholine receptor alpha 7 subunit stimulator such as ATA-101/bradanicline; codeine, gabapentin, pregablin, or azithromycin. Anti-inflammatory agents are, for example, corticosteroids such as prednisolone or dexamethasone; cyclo-oxygenase-2 (COX2) inhibitors such as celecoxib, rofecoxib, parecoxib, valdecoxib, deracoxib, etoricoxib or lumiracoxib; prostaglandin E2 antagonists; leukotriene B4 antagonists; leukotriene D4 antagonists such as montelukast; 5-lipoxygenase inhibitors; or other nonsteroidal anti-inflammatory agents (NSAIDs) such as aspirin, diclofenac, diflunisal, etodolac, ibuprofen or indomethacin.

Anti-atopic dermatitis agents are, for example, cyclosporin, methotrexate, mycophenolate mofetil, azathioprine, phosphodiesterase inhibitors (e.g. apremilast, crisaborole), Janus Associated Kinase (JAK) inhibitors (e.g. tofacitinib), neutralizing antibodies against IL-4/IL13 (e.g. dupilamab), IL-13 (e.g. lebrikizumab, tralokinumab) and IL-31 (nemolizumab). Analgesics are, for example, of the opioid type, such as morphine, oxymorphine, levopanol, oxycodon, propoxyphene, nalmefene, fentanyl, hydrocondon, hydromorphone, meripidine, methadone, nalorphine, naloxone, naltrexone, buprenorphine, butorphanol, nalbuphine, pentazocine; or of the non-opioid type, such as acetophenamine.

Anti-depressants are, for example, tricyclic anti-depressants such as amitriptyline, clomipramine, despramine, doxepin, desipramine, imipramine, nortriptyline; selective serotonin reuptake inhibitor anti-depressants (SSRIs) such as fluoxetine, paroxetine, sertraline, citalopram, escitalopram; norepinephrine reuptake inhibitor anti-depressants (SNRIs) such as maprotiline, lofepramine, mirtazapine, oxaprotiline, fezolamine, tomoxetine, mianserin, buproprion, hydroxybuproprion, nomifensine, viloxazine; dual serotonin-norepinephrine reuptake inhibitor anti-depressants (SNRIs) such as duloxetine, venlafaxine, desvenlafaxine, levomilnacipran; atypical antidepressants such as trazodone, mirtazapine, vortioxetine, vilazodone, bupropion; or monoamine oxidase inhibitor anti-depressantss (MAOIs) such as tranylcypromine, phenelzine, or isocarboxazid.

Anxiolytics are, for example, benzodiazepines such as alprazolam, bromazepam, chlordiazepoxide, clonazepam, clorazepate, diazepam, flurazepam, lorazepam, oxazepam, temazepam, triazolam, or tofisopam; or they are nonbenzodiazepine hypnoticssuch as eszopiclone, zaleplon, zolpidem, or zopiclone; or they are carbamates e.g. meprobamate, carisoprodol, tybamate, or lorbamate; or they are antihistamines such as hydroxyzine, chlorpheniramine or diphenhydramine.

Sedatives are, for example, barbiturate sedatives, such as amobarbital, aprobarbital, butabarbital, butabital, mephobarbital, metharbital, methohexital, pentobarbital, secobarbital, talbutal, theamylal, or thiopental; or they are non-barbiturate sedatives such as glutethimide, meprobamate, methaqualone or dichloalphenazone.

Skeletal muscle relaxants are, for example, baclofen, meprobamate, carisoprodol, cyclobenzaprine, metaxalone, methocarbamol, tizanidine, chlorzoxazone or orphenadrine.

Other suitable combination partners are inhibitors of Acetylcholinesterase inhibitors such as donepezil; 5-HT-3 anatgonists such as ondansetron; metabotropic glutamate receptor antagonists; antiarrhythmics such as mexiletine or phenytoin; or NMDA receptor antagonists.

Further suitable combination partners are incontinence medications, for example, anticholinergics such as oxybutynin, tolterodine, darifenacin, fesoterodine, solifenacin or trospium; or they are bladder muscle relaxants such as mirabegron; or they are alpha blockers such as tamsulosin, alfuzosin, silodosin, doxazosin or terazosin.

The dosage for the combination partners mentioned above is usually 1/5 of the lowest dose normally recommended up to 1/1 of the normally recommended dose.

Therefore, in another aspect, this invention relates to the use of a compound according to the invention in combination with one or more additional therapeutic agents described hereinbefore and hereinafter for the treatment of diseases or conditions which may be affected or which are mediated by TRPA1, in particular diseases or conditions as described hereinbefore and hereinafter.

In a further aspect this invention relates to a method for treating a disease or condition which can be influenced by the inhibition of TRPA1 in a patient that includes the step of administering to the patient in need of such treatment a therapeutically effective amount of a compound of formula (I) or a pharmaceutically acceptable salt thereof in combination with a therapeutically effective amount of one or more additional therapeutic agents.

In a further aspect this invention relates to the use of a compound of formula (I) or a pharmaceutically acceptable salt thereof in combination with one or more additional therapeutic agents for the treatment of diseases or conditions which can be influenced by the inhibition of TRPA1 in a patient in need thereof.

In yet another aspect the present invention relates a method for the treatment of a disease or condition mediated by TRPA1 activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition that comprises a compound according to the invention and one or more additional therapeutic agents described hereinbefore and hereinafter, optionally together with one or more inert carriers and/or diluents.

In yet another aspect the present invention relates to the use of a compound according to the invention in a cough-measuring device.

Other features and advantages of the present invention will become apparent from the following more detailed examples which illustrate, by way of example, the principles of the invention.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples.

Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme I below.

Scheme I

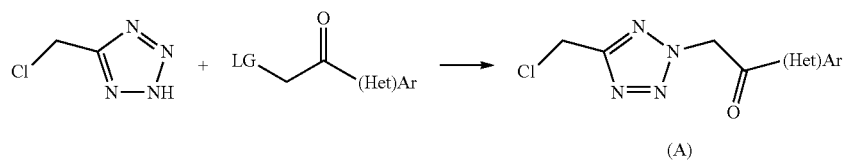

(A)

↓ [cat.]

-continued

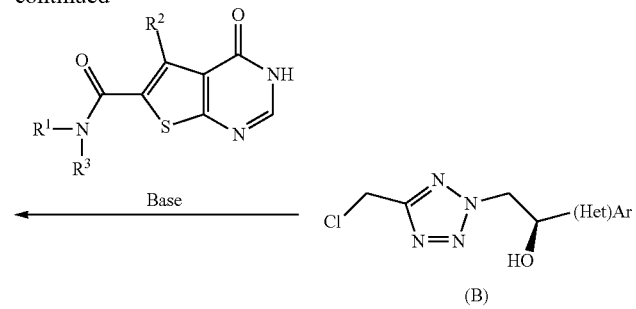

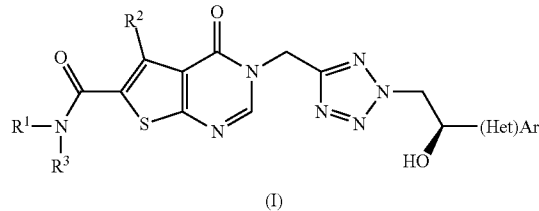

In scheme I, chloromethyltetrazole is N-alkylated with an appropriate aromatic or heteroaromatic acetophenone derivative carrying a leaving group "LG" (e.g. Cl or Br) alpha to the carbonyl group. The reaction can typically be run at ambient temperature or 50° C. in the presence of a base (e.g. $K_2CO_3$). The carbonyl group of side chain (A) can be reduced in an enantioselective fashion by using appropriate catalytic systems using a transition metal complex (of e.g. Ru or IR) in combination with a chiral ligand (e.g. ([(1S,2S)-(−)-2-amino-1,2-diphenylethyl](4-toluenesulfonyl)amido). In the presence of a base (e.g. $K_2CO_3$) side chain (B) can be used as alkylating agent for various thienopyrimidinones to afford the compounds of general formula (I).

Tricyclic thienopyrimidone compounds may be prepared as shown in Scheme II below.

Scheme II

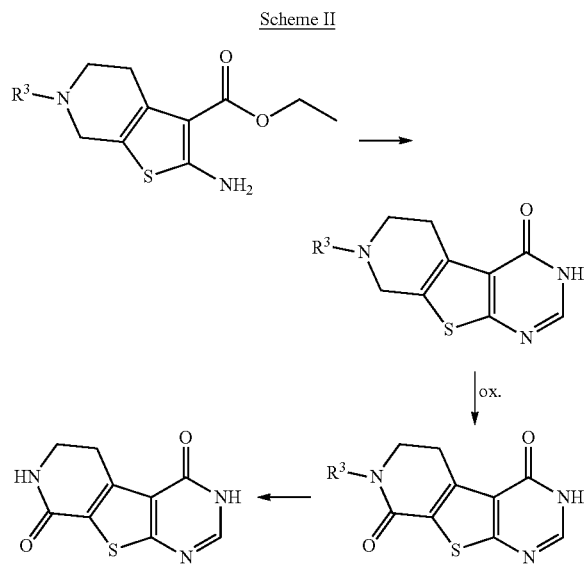

In scheme II, a suitable thieno-tetrahydropyridine precursor is converted with an appropriate reagent such as formamidine, formamide or a salt thereof in a suitable solvent (e.g. EtOH) at elevated temperatures (e.g. 100° C.) into the tricyclic thieno-pyrimidone compound (C). The tetrahydropyridine core is then oxidized using a suitable oxidant (e.g. $KMnO_4$) and is accelerated by the presence of a chelating reagent (e.g. 18-crown-6). This reaction is typically performed in a non-polar solvent (e.g. DCM) and run preferentially at ambient temperature. In case $R^3$ resembles a protecting group (e.g. BOC), this group can be removed using suitable conditions for deprotection (e.g. TFA/DCM or HCl/dioxane at RT for $R^3$=BOC).

EXAMPLES

Preparation

The compounds according to the invention and their intermediates may be obtained using methods of synthesis which are known to the one skilled in the art and described in the literature of organic synthesis for example using methods described in "Comprehensive Organic Transformations", 2nd Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled artisan but are not described in detail herein may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", 3rd Edition, Philip J. Kocienski, Thieme, 2005, and "Protective Groups in Organic Synthesis", 4th Edition, Peter G. M. Wuts, Theodora W. Greene, John Wiley & Sons, 2006. The terms "ambient temperature" and "room temperature" are used interchangeably and designate a temperature of about 20° C., e.g. between 19 and 24° C.

Abbreviations

| ACN | acetonitrile |
| Aq. | aqueous |
| ° C. | Degree celsius |
| CyH/CH | cyclohexane |
| conc. | concentrated |
| DCM | dichloro methane |

| | |
|---|---|
| DIPEA | N,N-diisopropylethylamine |
| DMA | N,N-dimethylacetamide |
| DMF | N,N-dimethylformamide |
| DMSO | dimethyl sulfoxide |
| ESI-MS | Electrospray ionisation mass spectrometry |
| EtOAc | ethyl acetate |
| EtOH | ethanol |
| ex | example |
| eq | equivalent |
| h | hour |
| HCl | Hydrochlorid acid |
| HPLC | High performance liquid chromatography |
| $K_2CO_3$ | potassium carbonate |
| L | liter |
| M | molar |
| MeOH | methanol |
| $MgSO_4$ | magnesium sulphate |
| min | minute |
| mL | milliliter |
| MTBE | tert-butylmethylether |
| n.d. | not determined |
| $NH_3$ | ammonia |
| RT | room temperature (about 20° C.) |
| sat. | saturated |
| TBTU | Benzotriazolyl tetramethyluronium tetrafluoroborate |
| TEA | triethylamine |
| TFA | trifluoroacetic acid |
| THF | tetrahydrofuran |

Preparation of Starting Compounds

Intermediate I

Intermediate 1.1 (General Route)

1-(4-bromophenyl)-2-[5-(chloromethyl)-2H-1,2,3,4-tetrazol-2-yl]ethan-1-one

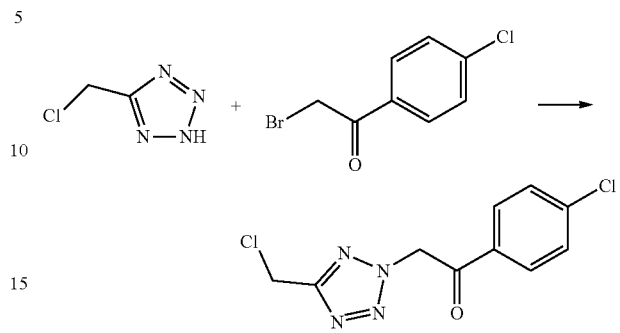

To 1.00 g (8.44 mmol) of 5-(chloromethyl)-2H-1,2,3,4-tetrazole and 2.17 g (9.28 mmol) 4-chlorophenacyl bromide in 15 mL DMA are added 1.63 g (11.8 mmol) $K_2CO_3$. The reaction mixture is stirred at RT for 30 min and before the mixture is filtered. The solution is diluted with water and sat. aq. NaCl-solution and is extracted three times with EtOAc. The combined organic phase is washed with water, dried over $Na_2SO_4$, filtered over activated charcoal and the solvent is removed in vacuo. The residue is purified by column chromatography (silica gel; CH/EtOAc, 8/2→1/1).

$C_{10}H_8Cl_2N_4O$ (M=271.1 g/mol)

ESI-MS: 271 [M+H]$^+$ $R_f$ (HPLC): 1.01 min (method B)

The following compounds are prepared according to the general procedure (intermediate 1.1) described above:

| Int. | Starting materials | Structure | ESI-MS | HPLC retention time (method) [min] |
|---|---|---|---|---|
| I.2 | 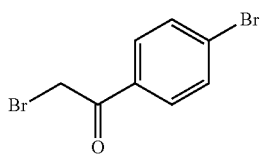 [SMILES: O=C(CBr)c1ccc(Br)cc1] | 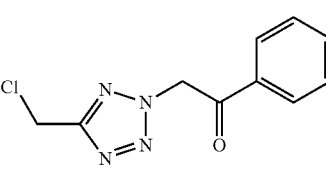 | 315/317 [M + H]$^+$ | 1.00 (C) |
| I.3 | 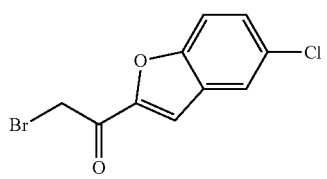 [SMILES: O=C(CBr)c1cc2cc(Cl)ccc2o1] | 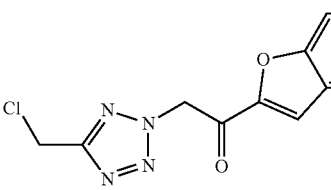 | 311 [M + H]$^+$ | 1.08 (C) |
| I.4 | 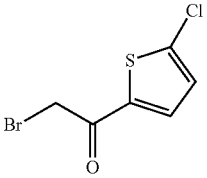 | 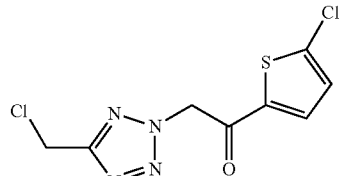 | 277 [M + H]$^+$ | 1.01 (C) |

| Int. | Starting materials | Structure | ESI-MS | HPLC retention time (method) [min] |
|---|---|---|---|---|
| I.5 | 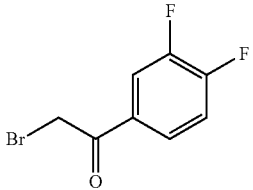 [SMILES: O=C(CBr)c1ccc(F)c(F)c1] | 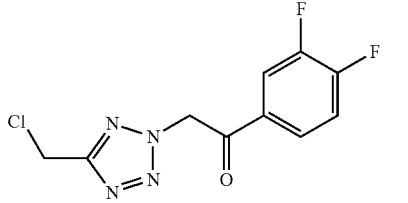 [SMILES: O=C(Cn1nnc(CCl)n1)c1ccc(F)c(F)c1] | 273 [M + H]⁺ | 1.00 (C) |
| I.6 | VII.1 | 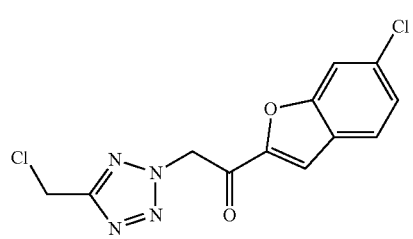 [SMILES: O=C(Cn1nnc(CCl)n1)c1cc2ccc(Cl)cc2o1] | 311 [M + H]⁺ | 1.02 (B) |
| I.7 | 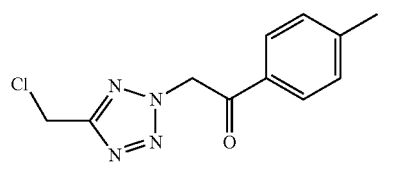 [SMILES: Cc1ccc(C(=O)Cn2nnc(CCl)n2)cc1] | 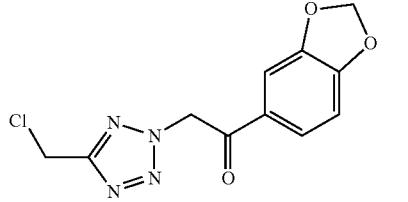 [SMILES: O=C(Cn1nnc(CCl)n1)c1ccc2c(c1)OCO2] | 251 [M + H]⁺ | 0.95 (C) |
| I.8 | 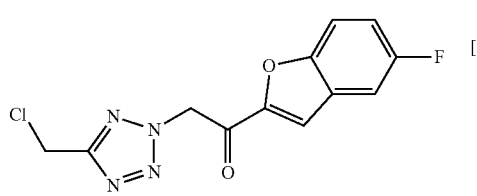 | 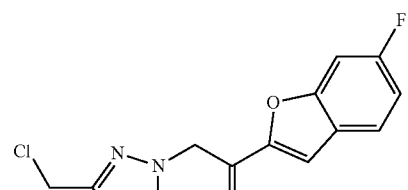 | 281 [M + H]⁺ | 0.89 (C) |
| I.9 | VII.2 | 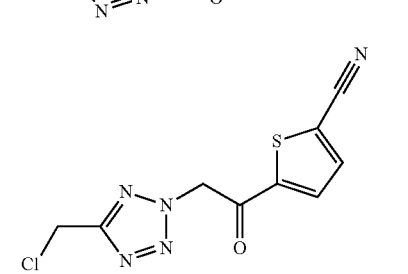 | 295 [M + H]⁺ | 1.02 (B) |
| I.10 | VII.3 | 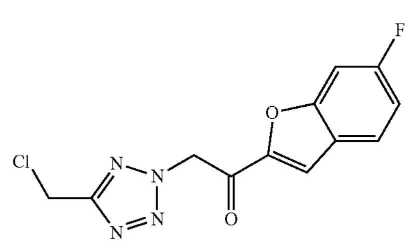 [SMILES: O=C(Cn1nnc(CCl)n1)c1cc2ccc(F)cc2o1] | 295 [M + H]⁺ | 1.02 (B) |
| I.11 | VII.4 | 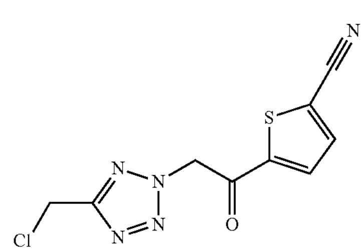 [SMILES: N#Cc1ccc(C(=O)Cn2nnc(CCl)n2)s1] | 268 [M + H]⁺ | 0.47 (G) |

| Int. | Starting materials | Structure | ESI-MS | HPLC retention time (method) [min] |
|---|---|---|---|---|
| I.12 | (structure with Br, benzothiophene, C=O) | (tetrazole-CH2Cl coupled product with benzothiophene) | 293 [M + H]+ | 1.12 (B) |

Intermediate II
Intermediate II.1 (General Route)

(1R)-1-(4-chlorophenyl)-2-[5-(chloromethyl)-2H-1,2,3,4-tetrazol-2-yl]ethan-1-ol

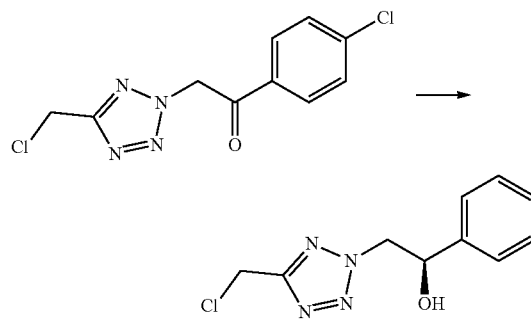

1.30 g (4.80 mmol) 1-(4-chlorophenyl)-2-[5-(chloromethyl)-2H-1,2,3,4-tetrazol-2-yl]ethan-1-one (example I.1) are added to 20 mL ACN under inert atmosphere. 11.9 mg (0.02 mmol) Chloro([(1S,2S)-(−)-2-amino-1,2-diphenylethyl](4-toluenesulfonyl)amido)(mesitylene)ruthenium (II) (CAS 174813-81-1) are added before 0.72 mL (1.73 mmol) formic acid triethylamine complex (5:2) are added dropwise. After stirring at RT for 3 h the solvent is removed in vacuo. To the remaining crude mixture is added water and this mixture is extracted with EtOAc. The organic layers are combined, dried over $Na_2SO_4$ and activated charcoal, filtered and the solvent is removed in vacuo.

$C_{10}H_{10}Cl_2N_4O$ (M=273.1 g/mol)

ESI-MS: 273 $[M+H]^+$ $R_t$ (HPLC): 0.96 min (method B)

The following compounds are prepared according to the general procedure (intermediate II.1) described above:

| Int. | Starting materials | Structure | ESI-MS | HPLC retention time (method) [min] |
|---|---|---|---|---|
| II.2 | I.2 | (tetrazole-CH2Cl with 4-bromophenyl-CH(OH)-) | 317/319 [M + H]+ | 1.14 (B) |
| II.3 | I.3 | (tetrazole-CH2Cl with chloro-benzofuran-CH(OH)-) | 313 [M + H]+ | 1.03 (B) |
| II.4 | I.4 | (tetrazole-CH2Cl with chlorothiophene-CH(OH)-) | 279 [M + H]+ | 0.97 (C) |

-continued

| Int. | Starting materials | Structure | ESI-MS | HPLC retention time (method) [min] |
|---|---|---|---|---|
| II.5 | I.5 | 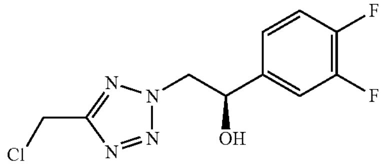 [SMILES: O[C@@H](Cn1nnc(CCl)n1)c1ccc(F)c(F)c1] | 275 [M + H]+ | 0.48 (A) |
| II.6 | I.6 | 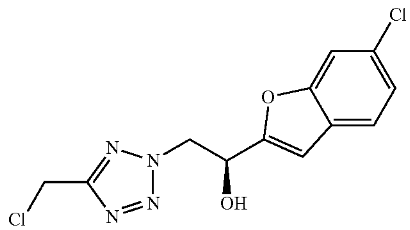 [SMILES: O[C@@H](Cn1nnc(CCl)n1)c1cc2ccc(Cl)cc2o1] | 313 [M + H]+ | 1.01 (B) |
| II.7 | I.7 | 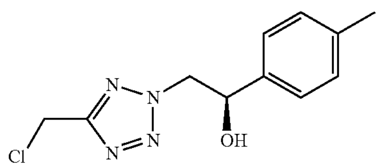 [SMILES: Cc1ccc([C@@H](O)Cn2nnc(CCl)n2)cc1] | 253 [M + H]+ | 0.48 (A) |
| II.8 | I.8 | 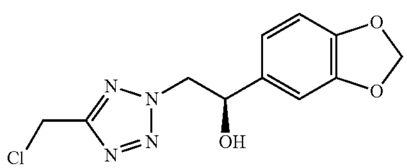 [SMILES: O[C@@H](Cn1nnc(CCl)n1)c1ccc2c(c1)OCO2] | 283 [M + H]+ | 0.43 (A) |
| II.9 | I.9 | 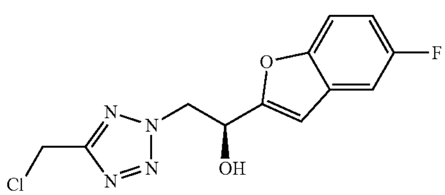 [SMILES: O[C@@H](Cn1nnc(CCl)n1)c1cc2cc(F)ccc2o1] | 297 [M + H]+ | 0.97 (B) |
| II.10 | I.10 | 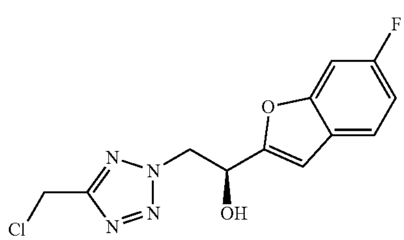 [SMILES: O[C@@H](Cn1nnc(CCl)n1)c1cc2ccc(F)cc2o1] | 297 [M + H]+ | 0.97 (B) |
| II.11 | I.11 | 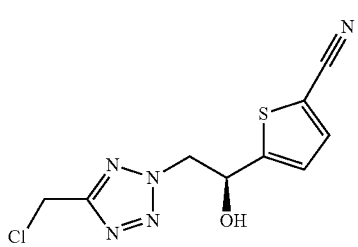 [SMILES: N#Cc1ccc([C@@H](O)Cn2nnc(CCl)n2)s1] | 270 [M + H]+ | 0.41 (A) |

| Int. | Starting materials | Structure | ESI-MS | HPLC retention time (method) [min] |
|---|---|---|---|---|
| II.12 | I.12 | 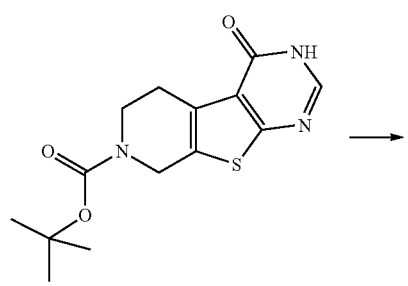 | 295 [M + H]⁺ | 1.10 (B) |

Intermediate III
Intermediate III.1 (General Route)

tert-butyl 4,8-dioxo-5,6-dihydro-3H-pyrido[2,3]
thieno[2,4-c]pyrimidine-7-carboxylate

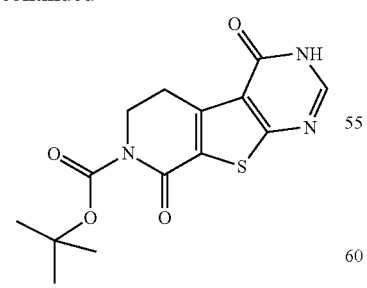

500 mg (1.63 mmol) tert-butyl 4-oxo-3,5,6,8-tetrahydro-pyrido[2,3]thieno[2,4-c]pyrimidine-7-carboxylate, 514 mg (3.25 mmol) potassium permanganate, 86.0 mg (0.33 mmol) 18-crown-6 are added to 8 mL DCM. The reaction mixture is stirred at RT overnight. The mixture is diluted with MeOH and with 10% sodium metabisulfite solution. The precipitate is filtered off and the solution is evaporated. The crude residue is suspended in MeOH/DMF, filtered and purified by HPLC (ACN/H$_2$O/TFA gradient).

$C_{14}H_{15}N_3O_4S$ (M=321.4 g/mol)
ESI-MS: 322 [M+H]⁺
R$_t$ (HPLC): 0.45 min (method A)

The following compounds are prepared according to the general procedure (example III.1) described above:

| Ex. | Starting materials | Structure | ESI-MS | HPLC retention time (method) [min] |
|---|---|---|---|---|
| III.2 | V.1 | 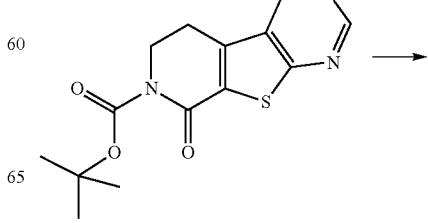 | 236 [M + H]⁺ | 0.27 (A) |

Intermediate IV
Intermediate IV.1 (General Route)

6,7-dihydropyrido[4',3':4,5]thieno[2,3-d]pyrimidine-4,8(3H,5H)-dione

-continued

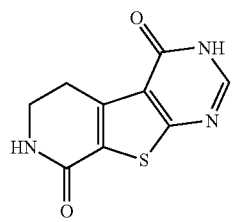

14.0 mg (0.04 mmol) tert-butyl 4,8-dioxo-5,6-dihydro-3H-pyrido[2,3]thieno[2,4-c]pyrimidine-7-carboxylate (example III.1) in 500 µL DCM is treated with 35 µL (0.45 mmol) TFA. The reaction mixture is stirred at RT for 0.5 h and the mixture is concentrated to give the desired product that was used in the next step without further purification.

$C_9H_7N_3O_2S$ (M=221.2 g/mol)
ESI-MS: 222 $[M+H]^+$
$R_t$ (HPLC): 0.22 min (method A)
Intermediate V
Intermediate V.I (general route)

7-methyl-3,5,6,8-tetrahydropyrido[2,3]thieno[2,4-c]pyrimidin-4-one

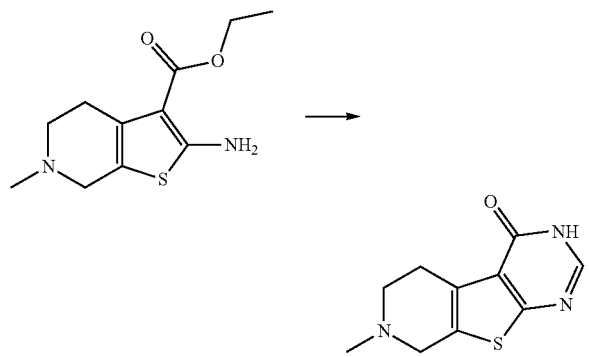

1.00 g (4.00 mmol) ethyl 2-amino-6-methyl-4,5,6,7-tetrahydrothieno[2,3-c]pyridine-3-carboxylate in 10 mL EtOH is treated with 2.89 mL (31.0 mmol) formamidine acetate. The reaction mixture is stirred at 100° C. for 6 h. After that, 0.58 mL (19.0 mmol) formamidine acetate is added and the mixture is stirred another 4 h at 100° C. After cooling to ambient temperature, the product is filtered off and is washed with ethanol. The collected precipitate is dried in an oven at 50° C.

$C_{10}H_{11}N_3OS$ (M=221.3 g/mol)
ESI-MS: 222 $[M+H]^+$
$R_t$ (HPLC): 0.15 min (method A)
Intermediate VI
Intermediate VI.1 (General Route)

1-(6-chloro-1-benzofuran-2-yl)ethan-1-one

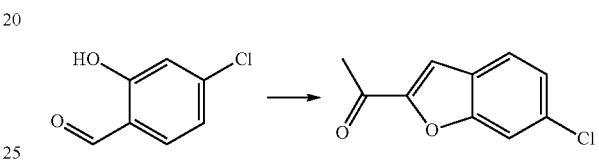

1.00 g (6.39 mmol) 4-chloro-2-hydroxybenzaldehyde in 10 mL acetone under argon is treated with 0.56 mL (7.03 mmol) chloroacetone in 10 mL acetone is treated with 1.47 g (10.6 mmol) potassium carbonate and 2.89 mL (31.0 mmol) formamidine acetate under argon. The reaction mixture is stirred 3 h at 70° C. The reaction mixture is cooled down, the precipitate is filtered off and the solution is evaporated. The residue is recrystallized in 10 mL ice cold MeOH, the crystals are filtered off and dried overnight.

$C_{10}H_7ClO_2$ (M=194.6 g/mol)
EI-MS: 194 $[M^*]^+$
$R_t$ (HPLC): 1.02 min (method B)

The following compounds are prepared according to the general procedure (intermediate VI.1) described above:

| Int. | Starting materials | Structure | ESI-MS | HPLC retention time (method) [min] |
|---|---|---|---|---|
| VI.2 | | 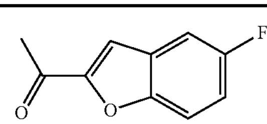 | 179 $[M + H]^+$ | 0.95 (B) |
| VI.3 | | 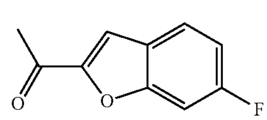 | 179 $[M + H]^+$ | 0.95 (B) |

Intermediate VII
Intermediate VII.1 (General Route)

2-bromo-1-(6-chloro-1-benzofuran-2-yl)ethan-1-one

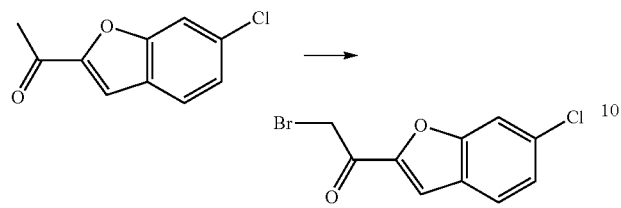

840 mg (4.32 mmol) 1-(6-chloro-1-benzofuran-2-yl)ethan-1-one (example VI.1) in 10 mL THF is treated with 2.08 g (4.32 mmol) tetrabutylammonium tribromide, dissolved in 500 µL MeOH and 5 mL THF, dropwise. The reaction mixture is stirred for 1 h at RT. The reaction mixture is evaporated, the residue is diluted with water/1M HCl and is extracted with MTBE. The organic phases are combined, washed with 1M HCl and water, dried over MgSO4, filtered and the solvent is removed in vacuo. The residue is purified by column chromatography (silica gel; CH/EtOAc, 95/5 to 50/50).
C$_{10}$H$_6$BrClO$_2$ (M=273.5 g/mol)
ESI-MS: 273/275 [M+H]$^+$
R$_t$ (HPLC): 1.10 min (method B)
The following compounds are prepared according to the general procedure (intermediate VII.1) described above:

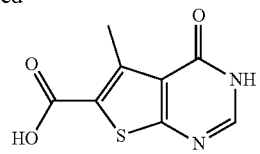

2.00 g (8.92 mmol) methyl 5-methyl-4-oxo-3H,4H-thieno[2,3-d]pyrimidine-6-carboxylate in 25 mL MeOH is treated with 6.69 mL (26.8 mmol) 4M aq. NaOH solution. The reaction mixture is stirred at RT for 2 h. The solution is then acidified by adding 4M aq. HCl solution, the crystals are filtered, washed with water and dried in the oven at 60° C. to give the desired product.
C$_8$H$_6$N$_2$O$_3$S (M=210.2 g/mol)
ESI-MS: 211 [M+H]$^+$
R$_t$ (HPLC): 0.29 min (method E)

| Int. | Starting materials | Structure | ESI-MS | HPLC retention time (method) [min] |
|---|---|---|---|---|
| VII..2 | VI.2 | 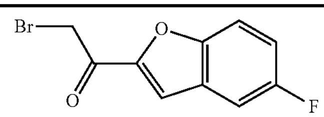 | 257/259 [M + H]$^+$ | 1.03 (B) |
| VII..3 | VI.3 | 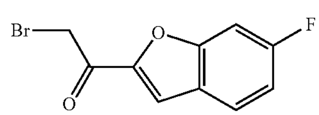 [SMILES: O=C(CBr)c1cc2ccc(F)cc2o1] | Mass not detected | 1.03 (B) |
| VII.4* | | 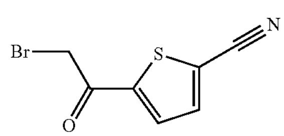 [SMILES: N#Cc1ccc(C(=O)CBr)s1] | 228/230 [M − H]$^-$ | 0.75 (H) |

*The reaction is performed with bromine (13.6 eq) at RT for 2 h in dioxane/diethyl ether and quenched with sodium thiosulfate solution.

Intermediate VIII
Intermediate VIII.1 (General Route)

5-methyl-4-oxo-3H,4H-thieno[2,3-d]pyrimidine-6-carboxylic acid

Intermediate IX
Intermediate IX. 1 (General Route)

N,5-dimethyl-4-oxo-3H,4H-thieno[2,3-d]pyrimidine-6-carboxamide

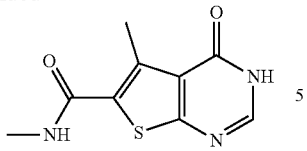

250 mg (1.19 mmol) 5-methyl-4-oxo-3H,4H-thieno[2,3-d]pyrimidine-6-carboxylic acid (example VIII.1) in 30 mL THF is treated with 429 mg (1.19 mmol) TBTU and 331 μL (2.38 mmol) TEA. The reaction mixture is stirred at RT for 30 min before 654 μL (1.31 mmol) methylamine (2M solution in THF) is added to the solution. The reaction mixture is stirred at RT overnight. The reaction mixture is evaporated, the residue is extracted with DCM/water, the organic phases are combined, dried, filtered and the solvent is removed in vacuo. The residue is purified by column chromatography (silica gel; DCM/MeOH/NH₃ 90/10/1).

$C_9H_9N_3O_2S$ (M=223.3 g/mol)

ESI-MS: 224 [M+H]⁺

$R_t$ (HPLC): 0.62 min (method C)

Intermediate X

Intermediate X.1 (General Route)

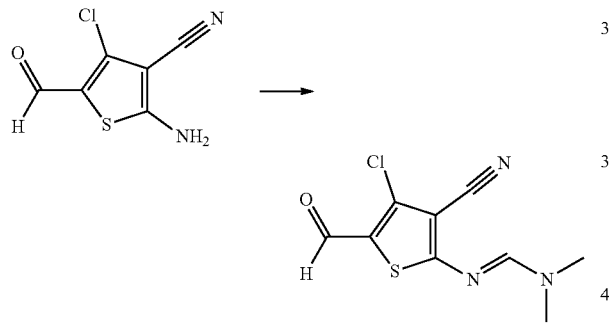

To 5.00 g (26.8 mmol) 2-amino-4-chloro-3-cyano-5-formylthiophene (CAS: 104366-23-6) in 25 mL pyridine is added 5.70 mL (42.9 mmol) N,N-dimethylformamide dimethyl acetal. The mixture is stirred at 100° C. for 3 h. After cooling to ambient temperature, the mixture is concentrated under reduced pressure. The residue is resuspended in DCM and washed with water. The organic phase is dried over Na₂SO₄ and concentrated to yield the desired product.

$C_9H_8ClN_3OS$ (M=241.7 g/mol)

ESI-MS: 242 [M+H]⁺

$R_t$ (HPLC): 1.04 min (method B)

Intermediate XI

Intermediate XI.1 (general route)

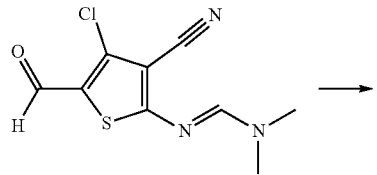

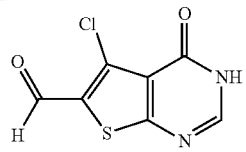

To 1.00 g (4.14 mmol) of example X.1 in 10 mL formic acid is added 678 mg (8.27 mmol) sodium acetate. The reaction mixture is stirred at reflux overnight. After cooling to ambient temperature, the mixture is poured onto ice-cold water. It is then diluted with dichloromethane and concentrated to dryness. The residue is suspended in dichloromethane and the remaining salts are filtered off. The filtrate is concentrated to yield the desired product.

$C_7H_3ClN_2O_2S$ (M=214.6 g/mol)

ESI-MS: 213 [M−H]⁻

$R_t$ (HPLC): 0.87 min (method B)

Intermediate XII

Intermediate XII.1 (general route)

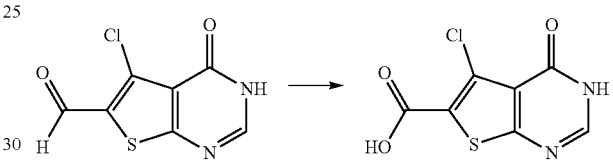

To 150 mg (699 μmol) of example XI.1 in 4.0 mL DMF is added 473 mg (769 μmol) potassium peroxymonosulfate. The reaction mixture is added at ambient temperature for 18 h.

The mixture is then purified by preparative HPLC (H₂O/ACN/TFA) to yield the desired product.

$C_7H_3ClN_2O_3S$ (M=230.6 g/mol)

ESI-MS: 229 [M−H]⁻

$R_t$ (HPLC): 0.58 min (method C)

Intermediate XIII

Intermediate XIII.1 (General Route)

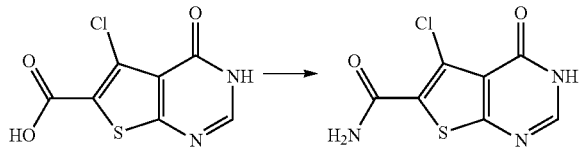 [SMILES: O=C(O)c1sc2nc[nH]c(=O)c2c1Cl ; NC(=O)c1sc2nc[nH]c(=O)c2c1Cl]

To 45.0 mg (0.195 mmol) of example XII.1 in 1.0 mL DMF is added 81.7 mg (0.215 mmol) 1-[Bis(dimethylamino)methylene]-1H-1,2,3-triazolo[4,5-b]pyridinium 3-oxid hexafluorophosphate, 74.8 μL (0.429 mmol) diisopropylethylamine and 1.17 mL (0.5 M, 0.585 mmol) of a solution of ammonia in THF. The reaction mixture is stirred at ambient temperature for 18 h. The reaction mixture is then purified by preparative HPLC (H₂O/ACN/NH₃ gradient) to yield the desired product.

$C_7H_4ClN_3O_2S$ (M=229.6 g/mol)

ESI-MS: 230 [M+H]⁺

$R_t$ (HPLC): 0.52 min (method C)

Preparation of Final Compounds

Example 1 (General Route)

3-({2-[(2R)-2-(4-chlorophenyl)-2-hydroxyethyl]-2H-1,2,3,4-tetrazol-5-yl}methyl)-5-methyl-4-oxo-3H,4H-thieno[2,3-d]pyrimidine-6-carboxamide

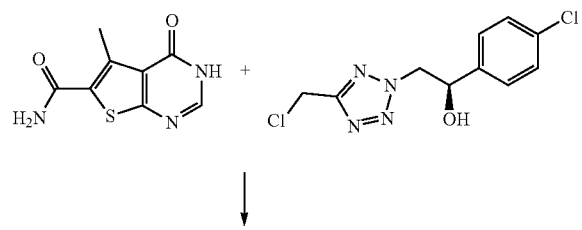

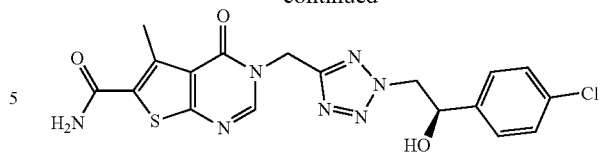

919 mg (4.39 mmol) of 5-Methyl-4-oxo-3H,4H-thieno[2,3-d]pyrimidine-6-carboxamide are added to 40 mL DMA. Then 1.97 g (14.3 mmol) $K_2CO_3$ and 1.20 g (4.39 mmol) of example II.1 are added and the mixture is stirred at 50° C. for 3 h. After cooling to RT, the mixture is purified by HPLC (ACN/$H_2$O/TFA gradient) to yield the desired product.

$C_{18}H_{16}ClN_7O_3S$ (M=445.9 g/mol)
ESI-MS: 446 [M+H]$^+$
$R_t$ (HPLC): 0.92 min (method B)
$^1$H NMR (400 MHz, DMSO-$d_6$) δ ppm: 2.70 (s, 3H), 4.73-4.82 (m, 2H), 5.12 (dt, J=7.4, 5.1 Hz, 1H), 5.49 (s, 2H), 5.91 (d, J=4.8 Hz, 1H), 7.33-7.41 (m, 4H), 7.67 (br s, 2H), 8.66 (s, 1H).

The following compounds are prepared according to the general procedure (example 1.1) described above:

| Ex. | Starting materials | Structure | Reaction conditions |
|---|---|---|---|
| 2 | II.2 + 5-Methyl-4-oxo-3H,4H-thieno[2,3-d]pyrimidine-6-carboxamide | 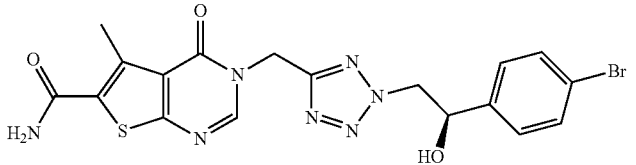 [SMILES: Cc1c(C(N)=O)sc2ncn(Cc3nnn(C[C@H](O)c4ccc(Br)cc4)n3)c(=O)c12] | Solvent: DMA, RT 20 h |
| 3 | II.3 + 5-Methyl-4-oxo-3H,4H-thieno[2,3-d]pyrimidine-6-carboxamide | 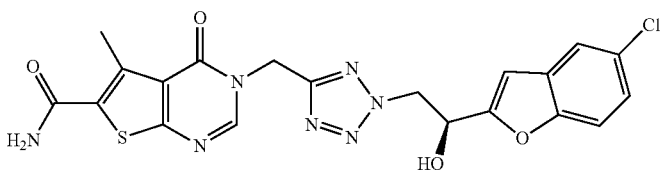 [SMILES: Cc1c(C(N)=O)sc2ncn(Cc3nnn(C[C@H](O)c4cc5cc(Cl)ccc5o4)n3)c(=O)c12] | Solvent: DMF; |
| 4 | II.4 + 5-Methyl-4-oxo-3H,4H-thieno[2,3-d]pyrimidine-6-carboxamide | 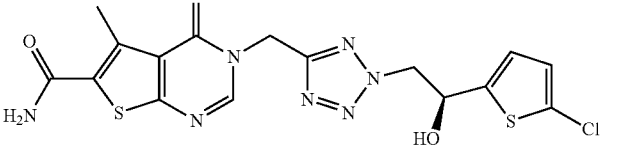 | Solvent: DMF; directly purified by HPLC |
| 5 | II.5 + 5-Methyl-4-oxo-3H,4H-thieno[2,3-d]pyrimidine-6-carboxamide | 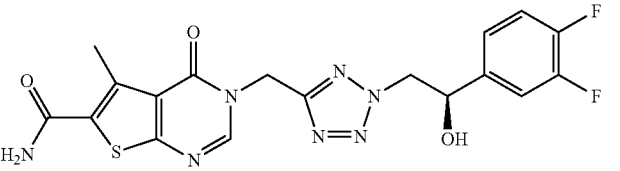 [SMILES: Cc1c(C(N)=O)sc2ncn(Cc3nnn(C[C@H](O)c4ccc(F)c(F)c4)n3)c(=O)c12] | Solvent: DMF; directly purified by HPLC |
| 6 | II.2 + IV.1 | 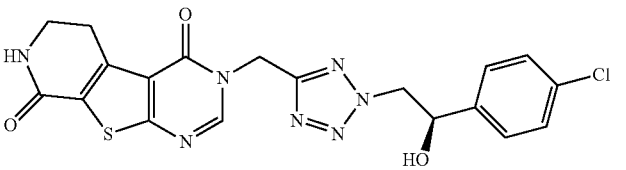 [SMILES: O=C1NCCc2c1sc1ncn(Cc3nnn(C[C@H](O)c4ccc(Cl)cc4)n3)c(=O)c21] | 3.2 eq II.2, 6.1 eq base; 3 h RT |

-continued

| Ex. | Starting materials | Structure | Reaction conditions |
|---|---|---|---|
| 7 | II.2 + III.2 | 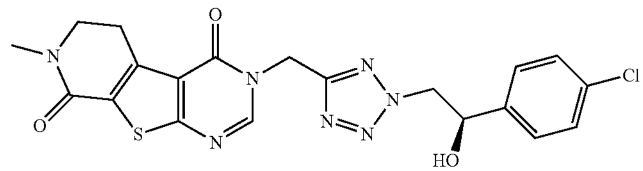 [SMILES: CN1CCc2c(sc3ncn(Cc4nnn(C[C@H](O)c5ccc(Cl)cc5)n4)c(=O)c23)C1=O] | Solvent: DMF; 3 h RT; 2 h 50° C. |
| 8 | II.6 + 5-Methyl-4-oxo-3H,4H-thieno[2,3-d]pyrimidine-6-carboxamide | 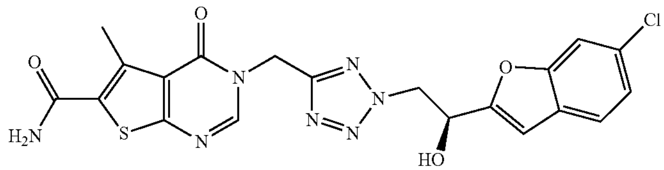 [SMILES: Cc1c(C(N)=O)sc2ncn(Cc3nnn(C[C@H](O)c4cc5ccc(Cl)cc5o4)n3)c(=O)c12] | Solvent: DMF; 3 h 50° C.; directly purified by HPLC |
| 9 | II.7 + 5-Methyl-4-oxo-3H,4H-thieno[2,3-d]pyrimidine-6-carboxamide | 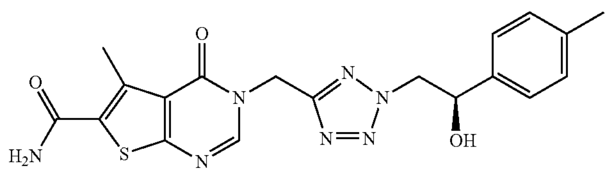 [SMILES: Cc1ccc([C@@H](O)Cn2nnc(Cn3cnc4sc(C(N)=O)c(C)c4c3=O)n2)cc1] | Solvent: DMF; overnight RT; directly purified by HPLC |
| 10 | II.8 + 5-Methyl-4-oxo-3H,4H-thieno[2,3-d]pyrimidine-6-carboxamide | 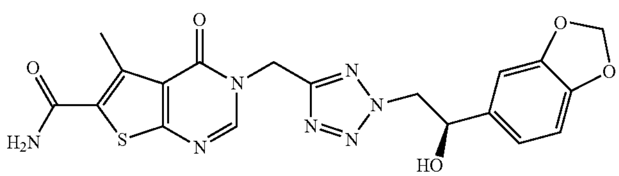 [SMILES: Cc1c(C(N)=O)sc2ncn(Cc3nnn(C[C@H](O)c4ccc5c(c4)OCO5)n3)c(=O)c12] | Solvent: DMF; 2 h RT; directly purified by HPLC |
| 11 | II.9 + 5-Methyl-4-oxo-3H,4H-thieno[2,3-d]pyrimidine-6-carboxamide | 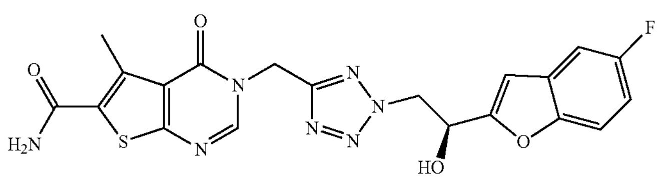 [SMILES: Cc1c(C(N)=O)sc2ncn(Cc3nnn(C[C@H](O)c4cc5cc(F)ccc5o4)n3)c(=O)c12] | 3 h 50° C.; overnight RT; directly purified by HPLC |
| 12 | II.10 + 5-Methyl-4-oxo-3H,4H-thieno[2,3-d]pyrimidine-6-carboxamide | 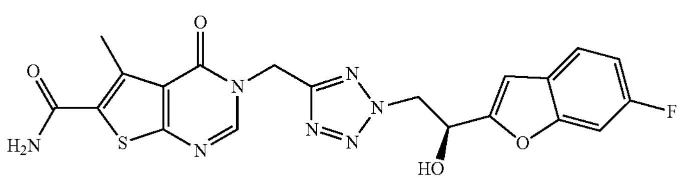 [SMILES: Cc1c(C(N)=O)sc2ncn(Cc3nnn(C[C@H](O)c4cc5ccc(F)cc5o4)n3)c(=O)c12] | 3 h 50° C.; RT overnight; directly purified by HPLC |
| 13 | II.2 + iX.1 | 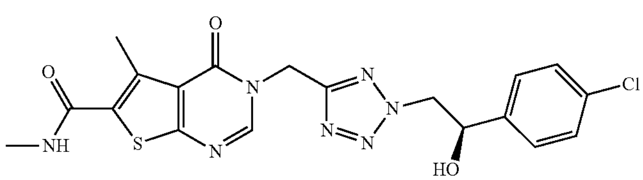 [SMILES: CNC(=O)c1sc2ncn(Cc3nnn(C[C@H](O)c4ccc(Cl)cc4)n3)c(=O)c2c1C] | Solvent: DMF; 3 h RT; directly purified by HPLC |
| 14 | II.8 + IX.1 | 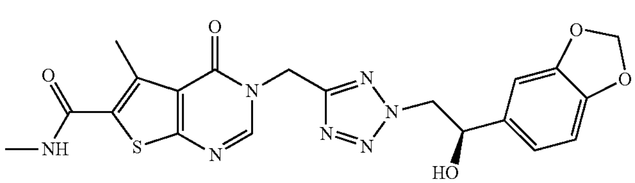 [SMILES: CNC(=O)c1sc2ncn(Cc3nnn(C[C@H](O)c4ccc5c(c4)OCO5)n3)c(=O)c2c1C] | Solvent: DMF; 2 h RT; directly purified by HPLC |

-continued

| Ex. | Starting materials | Structure | Reaction conditions |
|---|---|---|---|
| 15 | II.7 + IX.1 | 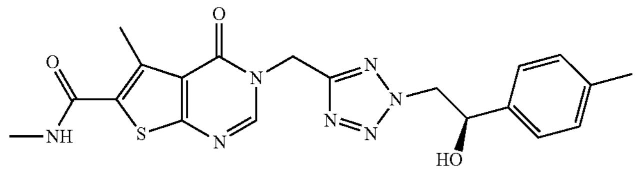 | Solvent: DMF; 2 h RT; directly purified by HPLC |
| 16 | II.4 + IX.1 | 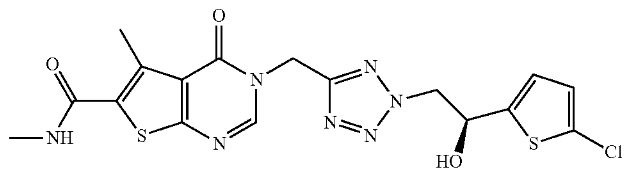 [SMILES: CNC(=O)c1sc2ncn(Cc3nnn(C[C@H](O)c4ccc(Cl)s4)n3)c(=O)c2c1C] | Solvent: DMF; 2 h RT; directly purified by HPLC |
| 17 | II.4 + IV.1 | 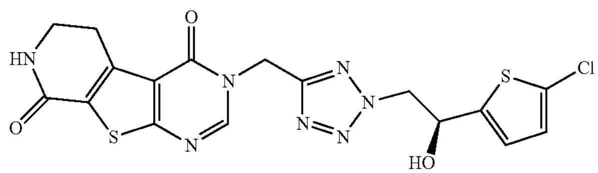 [SMILES: O=C1NCCc2c1sc1ncn(Cc3nnn(C[C@H](O)c4ccc(Cl)s4)n3)c(=O)c21] | DMF, RT, 18 h; directly purified by HPLC |
| 18 | II.3 + IV.1 | 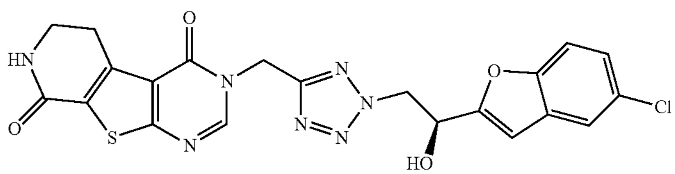 [SMILES: O=C1NCCc2c1sc1ncn(Cc3nnn(C[C@H](O)c4cc5cc(Cl)ccc5o4)n3)c(=O)c21] | DMF, RT, 18 h; directly purified by HPLC |
| 19 | II.9 + IV.1 | 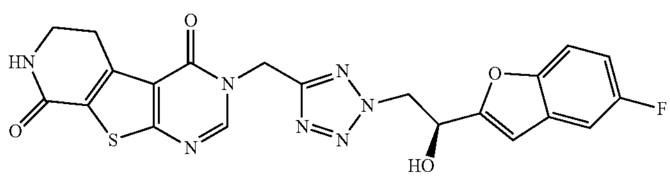 [SMILES: O=C1NCCc2c1sc1ncn(Cc3nnn(C[C@H](O)c4cc5cc(F)ccc5o4)n3)c(=O)c21] | DMF, RT, 5.5 h; directly purified by HPLC |
| 20 | II.7 + IV.1 | 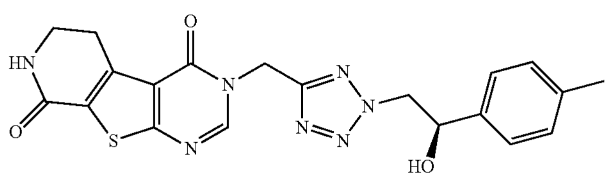 [SMILES: Cc1ccc([C@@H](O)Cn2nnc(Cn3cnc4sc5c(c4c3=O)CCNC5=O)n2)cc1] | DMF, RT, 19 h; directly purified by HPLC |
| 21 | II.11 + IV.1 | 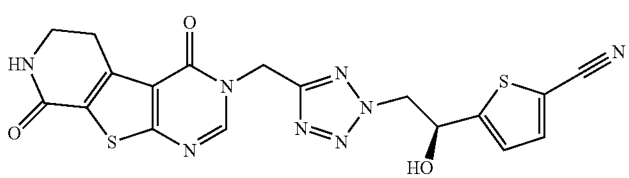 [SMILES: N#Cc1ccc([C@@H](O)Cn2nnc(Cn3cnc4sc5c(c4c3=O)CCNC5=O)n2)s1] | DMF, RT, 18 h; directly purified by HPLC |
| 22 | II.12 + 5-Methyl-4-oxo-3H,4H-thieno[2,3-d]pyrimidine-6-carboxamide | 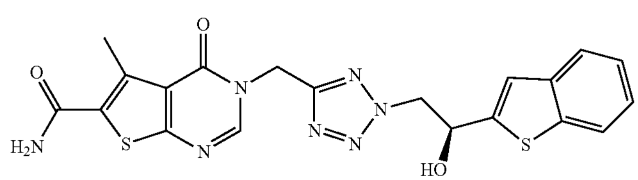 [SMILES: Cc1c(C(N)=O)sc2ncn(Cc3nnn(C[C@H](O)c4cc5ccccc5s4)n3)c(=O)c12] | DMF, 3 h 50° C., overnight RT; directly purified by HPLC |

-continued

| Ex. | Starting materials | Structure | Reaction conditions |
|---|---|---|---|
| 23 | II.2 + XIII.1 | (structure: 5-chloro-4-oxo-thieno[2,3-d]pyrimidine-6-carboxamide linked via CH₂ to tetrazole N-substituted with CH₂-CH(OH)-(4-chlorophenyl)) | DMF, 18 h RT; directly purified by HPLC |

Analytical data for the compounds described in the table above:

| Ex. | ESI-MS | HPLC retention time (method) [min] | $^1$H NMR (400 MHz, DMSO-$d_6$) δ ppm |
|---|---|---|---|
| 2 | 490/492 [M + H]$^+$ | 1.02 (B) | 2.70 (s, 3H), 4.73-4.83 (m, 2H), 5.10 (dd, J = 7.5, 5.3 Hz, 1H), 5.49 (s, 2 H), 5.95 (br s, 1H), 7.29-7.35 (m, 2H), 7.47-7.52 (m, 2H), 7.67 (s, 2H), 8.66 (s, 1H). |
| 3 | 486 [M + H]$^+$ | 0.63 (D) | 2.69 (s, 3H), 4.97-5.08 (m, 2H), 5.27 (dt, J = 7.6, 5.5 Hz, 1H), 5.48 (s, 2H), 6.29 (d, J = 5.8 Hz, 1H), 6.82 (s, 1H), 7.30 (dd, J = 8.7, 2.3 Hz, 1H), 7.58 (d, J = 8.6 Hz, 1H), 7.63-7.69 (m, 3H), 8.63 (s, 1H) |
| 4 | 452 [M + H]$^+$ | 0.87 (C) | 2.69 (s, 3H), 4.81 (dd, J = 13.6, 8.1 Hz, 1H), 4.89 (dd, J = 13.7, 4.6 Hz, 1H), 5.25-5.32 (m, 1H), 5.50 (s, 2H), 6.39 (d, J = 5.3 Hz, 1H), 6.86 (dd, J = 3.8, 0.8 Hz, 1H), 6.93 (d, J = 3.8 Hz, 1H), 7.66 (s, 2H), 8.66 (s, 1H) |
| 5 | 448 [M + H]$^+$ | 0.84 (C) | 2.69 (s, 3H), 4.75-4.85 (m, 2H), 5.13 (dd, J = 7.4, 5.3 Hz, 1H), 5.49 (s, 2H), 5.98 (br s, 1H), 7.18-7.24 (m, 1H), 7.35 (dt, J = 10.7, 8.4 Hz, 1H), 7.45 (ddd, J = 11.7, 7.9, 2.0 Hz, 1H), 7.66 (s, 2H), 8.65 (s, 1H) |
| 6 | 458 [M + H]$^+$ | 0.44 (A) | δ ppm 3.12 (t, J = 7.0 Hz, 2H), 3.50 (td, J = 7.1, 2.5 Hz, 2H), 4.73-4.84 (m, 2H), 5.12 (dd, J = 7.4, 5.3 Hz, 1H), 5.51 (s, 2H), 6.28 (br s, 1H), 7.34-7.41 (m, 4H), 7.95 (br s, 1H), 8.70 (s, 1H) |
| 7 | 472 [M + H]$^+$ | 0.49 (A) | 2.99 (s, 3H), 3.20 (t, J = 7.2 Hz, 2H), 3.66 (t, J = 7.1 Hz, 2H), 4.72-4.83 (m, 2H), 5.12 (dd, J = 7.4, 5.5 Hz, 1H), 5.50 (s, 2H), 5.67-6.28 (br s, 1H), 7.31-7.45 (m, 4H), 8.69 (s, 1H) |
| 8 | 486 [M + H]$^+$ | 0.63 (D) | 2.68 (s, 3H), 4.99 (dd, J = 13.8, 7.5 Hz, 1H), 5.04 (dd, J = 13.8, 5.1 Hz, 1H), 5.26 (dt, J = 7.3, 5.4 Hz, 1H), 5.48 (s, 2H), 6.29 (d, J = 5.7 Hz, 1H), 6.85 (s, 1H), 7.27 (dd, J = 8.3, 1.8 Hz, 1H), 7.58 (d, J = 8.4 Hz, 1H), 7.66 (br s, 2H), 7.69-7.74 (m, 1H), 8.62 (s, 1H) |
| 9 | 426 [M + H]$^+$ | 0.41 (A) | 2.26 (s, 3H), 2.70 (s, 3H), 4.73 (d, J = 6.5 Hz, 2H), 5.05 (t, J = 6.5 Hz, 1H), 5.3-6.1 (br s, 1H), 5.49 (s, 1H), 7.08-7.13 (m, J = 7.9 Hz, 2H), 7.21-7.26 (m, J = 8.0 Hz, 2H), 7.66 (s, 2H), 8.65 (s, 1H) |
| 10 | 456 [M + H]$^+$ | 0.80 (C) | 2.69 (s, 3H), 4.71 (dd, J = 13.5, 5.2 Hz, 2H), 4.75 (dd, J = 13.6, 7.6 Hz, 1H), 5.02 (dt, J = 7.3, 5.1 Hz, 1H), 5.49 (s, 2H), 5.75 (d, J = 4.8 Hz, 1H), 5.96-5.99 (m, 2H), 6.78-6.83 (m, 2H), 6.98 (s, 1H), 7.66 (s, 2H), 8.65 (s, 1H) |
| 11 | 470 [M + H]$^+$ | 0.86 (B) | 2.68 (s, 3H), 4.95-5.08 (m, 2H), 5.27 (dd, J = 7.7, 4.8 Hz, 1H), 5.49 (s, 2H), 6.28 (br s, 1H), 6.83 (s, 1H), 7.11 (td, J = 9.2, 2.8 Hz, 1H), 7.39 (dd, J = 8.9, 2.7 Hz, 1H), 7.56 (dd, J = 9.0, 4.2 Hz, 1H), 7.68 (s, 2H), 8.63 (s, 1H) |
| 12 | 470 [M + H]+ | 0.56 (F) | 2.68 (s, 3H), 4.96-5.07 (m, 2H), 5.25 (dd, J = 7.6, 5.1 Hz, 1H), 5.49 (s, 2H), 5.88-6.67 (br s, 1H), 6.83 (s, 1H), 7.10 (td, J = 9.3, 2.3 Hz, 1H), 7.50 (dd, J = 9.3, 2.1 Hz, 1H), 7.58 (dd, J = 8.5, 5.6 Hz, 1H), 7.66 (s, 2H), 8.63 (s, 1H) |
| 13 | 460 [M + H]+ | 0.61 (D) | 2.67 (s, 3H), 2.77 (d, J = 4.6 Hz, 3H), 4.73-4.83 (m, 2H), 5.11 (t, J = 6.3 Hz, 1H), 5.49 (s, 2H), 5.91 (s, 1H), 7.33-7.42 (m, 4H), 8.16 (q, J = 4.1 Hz, 1H), 8.65 (s, 1H) |

-continued

| Ex. | ESI-MS | HPLC retention time (method) [min] | $^1$H NMR (400 MHz, DMSO-d$_6$) δ ppm |
|---|---|---|---|
| 14 | 470 [M + H]$^+$ | 0.84 (C) | 2.67 (s, 3H), 2.77 (d, J = 4.6 Hz, 3H), 4.71 (dd, J = 13.6, 5.4 Hz, 1H), 4.75 (dd, J = 13.7, 7.7 Hz, 1H), 5.02 (dd, J = 7.4, 5.6 Hz, 1H), 5.49 (s, 2H), 5.75 (br s, 1H), 5.97-5.99 (m, 2H), 6.81 (d, J = 0.9 Hz, 2H), 6.97-6.99 (m, 1H), 8.16 (q, J = 4.2 Hz, 1H), 8.66 (s, 1H) |
| 15 | 440 [M + H]$^+$ | 0.89 (C) | 2.26 (s, 3H), 2.67 (s, 3H), 2.77 (d, J = 4.6 Hz, 3H), 4.70-4.78 (m, 2H), 5.05 (t, J = 6.5 Hz, 1H), 5.33-6.10 (br s, 1H), 5.49 (s, 2H), 7.11 (d, J = 7.9 Hz, 2H), 7.24 (d, J = 8.0 Hz, 2H), 8.16 (q, J = 4.2 Hz, 1H), 8.65 (s, 1H) |
| 16 | 466 [M + H]$^+$ | 0.90 (C) | 2.67 (s, 3H), 2.77 (d, J = 4.6 Hz, 3H), 4.81 (dd, J = 13.6, 8.1 Hz, 1H), 4.89 (dd, J = 13.6, 4.6 Hz, 1H), 5.26-5.31 (m, 1H), 5.50 (s, 2H), 5.92-6.73 (br s, 1H), 6.86 (dd, J = 3.8, 0.9 Hz, 1H), 6.93 (d, J = 3.8 Hz, 1H), 8.16 (q, J = 4.3 Hz, 1H), 8.66 (s, 1H) |
| 17 | 464 [M + H]$^+$ | 0.44 (A) | 3.12 (t, J = 7.0 Hz, 2H), 3.49 (td, J = 7.0, 2.5 Hz, 2H), 4.82 (dd, J = 13.7, 8.2 Hz, 1H), 4.89 (dd, J = 13.7, 4.6 Hz, 1H), 5.29 (dd, J = 7.7, 4.5 Hz, 1H), 5.52 (s, 2H), 6.39 (br s, 1H), 6.87 (dd, J = 3.8, 0.8 Hz, 1H), 6.94 (d, J = 3.8 Hz, 1H), 7.92-7.97 (m 1H), 8.70 (s, 1H) |
| 18 | 498 [M + H]$^+$ | 0.48 (A) | 3.11 (t, J = 7.0 Hz, 2H), 3.50 (td, J = 7.1, 2.3 Hz, 2H), 4.97-5.08 (m, 2H), 5.28 (dd, J = 7.7, 4.8 Hz, 1H), 5.50 (s, 2H), 6.82 (s, 1H), 7.30 (dd, J = 8.7, 2.2 Hz, 1H), 7.58 (d, J = 8.7 Hz, 1H), 7.66 (d, J = 2.3 Hz, 1H), 7.92-7.98 (m, 1H), 8.67 (s, 1H) |
| 19 | 482 [M + H]$^+$ | 0.44 (A) | 3.11 (t, J = 7.0 Hz, 2H), 3.50 (td, J = 7.1, 2.5 Hz, 2H), 4.96-5.08 (m, 2H), 5.27 (dd, J = 7.7, 4.8 Hz, 1H), 5.50 (s, 2H), 6.28 (d, J = 5.7 Hz, 1H), 6.83 (s, 1H), 7.11 (td, J = 9.2, 2.7 Hz, 1H), 7.39 (dd, J = 8.9, 2.7 Hz, 1H), 7.56 (dd, J = 8.9, 4.1 Hz, 1H), 7.92-7.97 (m, 1H), 8.67 (s, 1H) |
| 20 | 438 [M + H]$^+$ | 0.43 (A) | 2.26 (s, 3 H), 3.12 (t, J = 7.0 Hz, 2H), 3.50 (td, J = 7.0, 2.5 Hz, 3H), 4.70-4.78 (m, 2H), 5.06 (t, J = 6.5 Hz, 1H), 5.52 (s, 2H), 5.54-5.99 (br s, 1H), 7.11 (d, J = 7.9 Hz, 2H), 7.24 (d, J = 8.0 Hz, 2H), 7.91-8.00 (m, 1H), 8.70 (s, 1H) |
| 21 | 455 [M + H]$^+$ | 0.36 (A) | 3.12 (t, J = 7.0 Hz, 2H), 3.50 (td, J = 7.1, 2.5 Hz, 2H), 4.88 (dd, J = 13.7, 8.0 Hz, 1H), 4.99 (dd, J = 13.8, 4.3 Hz, 1H), 5.46 (dd, J = 7.8, 3.9 Hz, 1H), 5.51 (s, 2H), 6.69 (br s, 1H), 7.18 (dd, J = 3.9, 0.9 Hz, 1H), 7.81 (d, J = 3.9 Hz, 1H), 7.95 (s, 1H), 8.69 (s, 1H) |
| 22 | 468 [M + H]$^+$ | 0.60 (D) | 2.70 (s, 3H), 4.91 (dd, J = 13.7, 8.4 Hz, 1H), 4.98 (dd, J = 13.7, 4.7 Hz, 1H), 5.46 (dd, J = 7.9, 4.6 Hz, 1H), 5.51 (s, 2 H), 6.43 (br s, 1H), 7.28-7.38 (m, 3H), 7.67 (s, 2H), 7.71-7.76 (m, 1H), 7.89-7.94 (m, 1H), 8.66 (s, 1H) |
| 23 | 466 [M + H]$^+$ | 0.84 (C) | 4.74-4.82 (m, 2H), 5.11 (dt, J = 7.1, 5.3 Hz, 1H), 5.50 (s, 2H), 5.92 (d, J = 4.9 Hz, 1H), 7.33-7.40 (m, 4H), 7.68 (br s, 1H), 8.13 (br s, 1H), 8.76 (s, 1H) |

Analytical HPLC Methods

Method A

| time (mm) | Vol % water (incl. 0.1% TFA) | Vol % ACN | Flow [mL/min] |
|---|---|---|---|
| 0.00 | 99 | 1 | 1.6 |
| 0.02 | 99 | 1 | 1.6 |
| 1.00 | 0 | 100 | 1.6 |
| 1.10 | 0 | 100 | 1.6 |

Analytical column: XBridge BEH C18_2.1 × 30 mm, 17 µm; column temperature: 60° C.

Method B

| time (mm) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm. 3.0 × 30 mm; column temperature: 60° C.

| Method C | | | |
|---|---|---|---|
| time (mm) | Vol % water (incl. 0.1% TFA) | Vol % ACN | Flow [mL/min] |
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 μm; 3.0 × 30 mm; column temperature: 60° C.

| Method D | | | |
|---|---|---|---|
| time (mm) | Vol. % water (incl. 0.1 % NH$_4$OH) | Vol. % ACN | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18_3.0 × 30 mm_2.5 μm (Waters); column temperature: 60° C.

| Method E | | | |
|---|---|---|---|
| time (mm) | Vol % water (incl. 0.1% TFA) | Vol. % ACN | Flow [mL/min] |
| 0.0 | 50.0 | 50.0 | 1.5 |
| 0.02 | 50.0 | 50.0 | 1.5 |
| 1.0 | 0.0 | 100.0 | 1.5 |
| 1.1 | 0.0 | 100.0 | 1.5 |

Analytical column: Sunfire (Waters) C18_2.1 × 30 mm_2.5 μm ;column temperature: 60° C.

| Method F | | | |
|---|---|---|---|
| time (mm) | Vol. % water (incl. 0.1 % NH$_4$OH) | Vol. % ACN | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18 (Waters) 2.5 μm; 3.0 × 30 mm; column temperature: 60° C.

| Method G | | | |
|---|---|---|---|
| time (mm) | Vol. % water (incl. 0.1 % TFA) | Vol. % ACN | Flow [mL/min] |
| 0.00 | 99 | 1 | 1.6 |
| 0.02 | 99 | 1 | 1.6 |
| 1.0 | 0 | 100 | 1.6 |
| 1.1 | 0 | 100 | 1.6 |

Analytical column: Zorbax StableBond C18 (Agilent) 1.8 μm; 2.1 × 30 mm; column temperature: 60° C.

| Method H | | | |
|---|---|---|---|
| time (mm) | Vol.% water (incl. 0.1 % TFA) | Vol. % ACN | Flow [mL/min] |
| 0.00 | 95 | 5 | 1.5 |
| 1.30 | 0 | 100 | 1.5 |
| 1.50 | 0 | 100 | 1.5 |

Analytical column: Sunfire C18 (Waters) 2.5 μm; 3.0 × 30 mm; column temperature: 60° C.

The invention claimed is:

1. A compound according to formula (I)

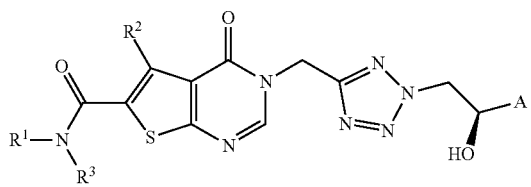

(I)

wherein

A is selected from the group consisting of phenyl, naphthyl, thiophenyl, benzothiophenyl and benzofuranyl, each optionally substituted with one or two members selected from the group consisting of H, F, Cl, Br, C$_{1-4}$-alkyl, F$_{1-3}$-fluoro-C$_{1-4}$-alkyl, —CN, —OCH$_3$, cyclopropyl, and cyclobutyl, or A is selected from

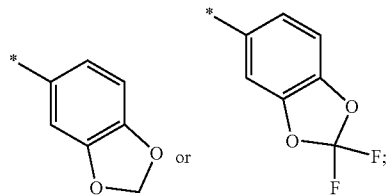 [SMILES: *c1ccc2c(c1)OCO2 ; *c1ccc2c(c1)OC(F)(F)O2]

and

R$^1$ is selected from H, C$_{1-4}$-alkyl, F$_{1-3}$-fluoro-C$_{1-4}$-alkyl, C$_{1-4}$-alkyl-OH or C$_{1-4}$-alkyl-CN;

R$^2$ is selected from C$_{1-2}$-alkyl or Cl;

or R$^1$ and R$^2$ are each CH$_2$ joined via a bond forming a 6-membered ring; and R$^3$ is selected from H, or C$_{1-4}$-alkyl;

or pharmaceutically acceptable salt thereof.

2. The compound of formula (I) according to claim 1, wherein A is selected from the group consisting of phenyl, thiophenyl and benzofuranyl, each optionally substituted with one or two members selected from the group consisting of H, F, Cl, Br, C$_{1-4}$-alkyl, F$_{1-3}$-fluoro-C$_{1-4}$-alkyl, CN, OCH$_3$, cyclopropyl, and cyclobutyl, or
A is selected from

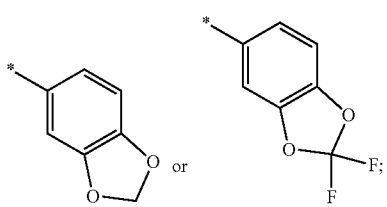 [SMILES: *c1ccc2c(c1)OCO2 ; *c1ccc2c(c1)OC(F)(F)O2]

or pharmaceutically acceptable salt thereof.

3. The compound of formula (I) according to claim 1, wherein A is selected from the group consisting of phenyl, thiophenyl and benzofuranyl, optionally substituted with one or two members selected from the group consisting of H, F, Br, Cl, and $CH_3$;
or
A is:

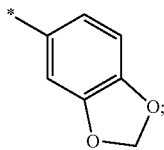 [SMILES: *c1ccc2c(c1)OCO2]

or pharmaceutically acceptable salt thereof.

4. The compound of formula (I) according to claim 1, wherein A is selected from the group consisting of

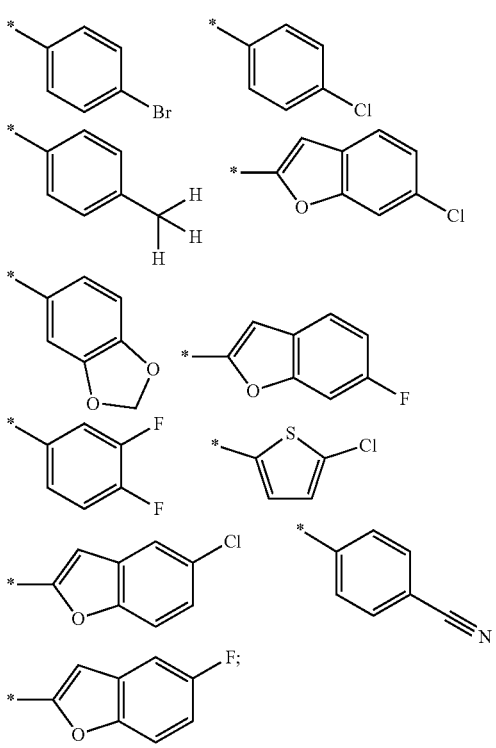

or pharmaceutically acceptable salt thereof.

5. The compound of formula (I) according to claim 1, wherein $R^1$ is selected from the group consisting of H and $C_{1-4}$-alkyl; or pharmaceutically acceptable salt thereof.

6. The compound of formula (I) according to claim 1, wherein $R^2$ is $CH_3$ or Cl; or pharmaceutically acceptable salt thereof.

7. The compound of formula (I) according to claim 1, wherein $R^3$ is H or $CH_3$; or pharmaceutically acceptable salt thereof.

8. The compound of formula (I) according to claim 1, selected from the group consisting of

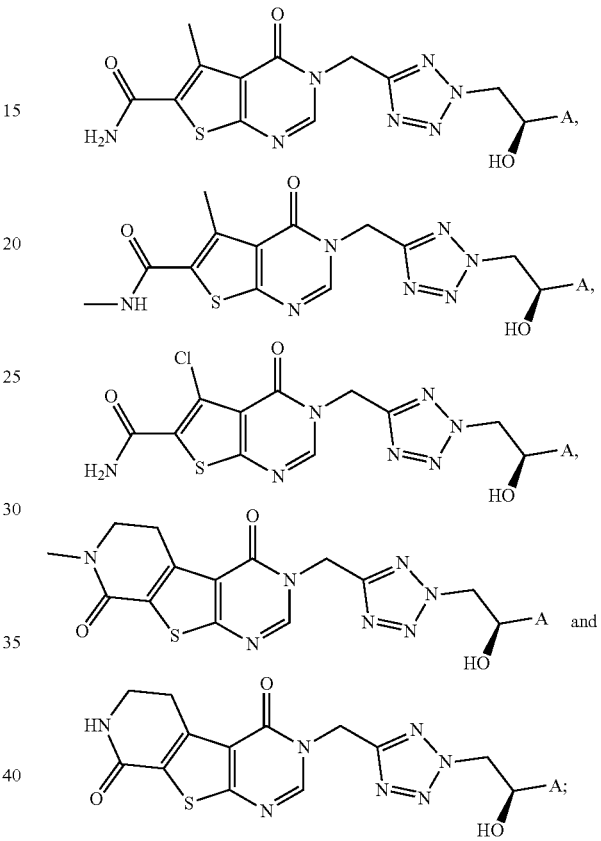

or pharmaceutically acceptable salt thereof.

9. The compound of formula (I) according to claim 1, selected from the group consisting of

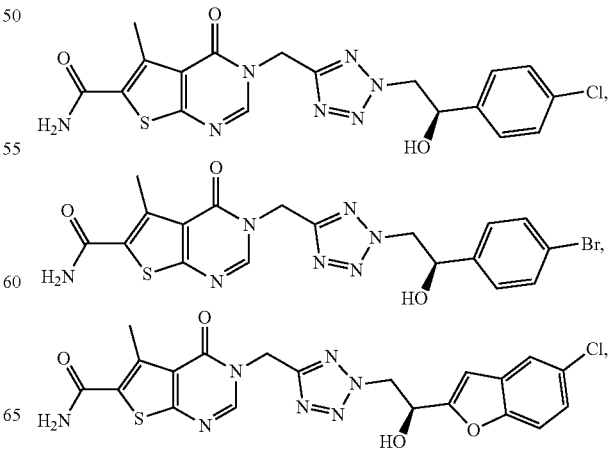

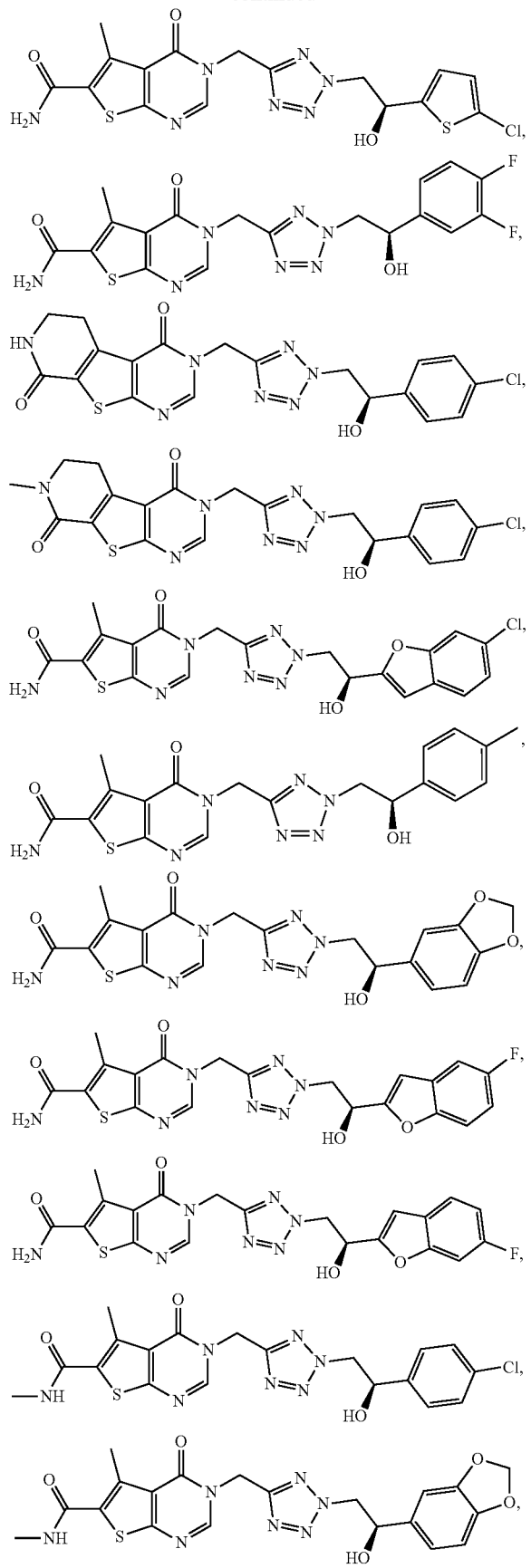
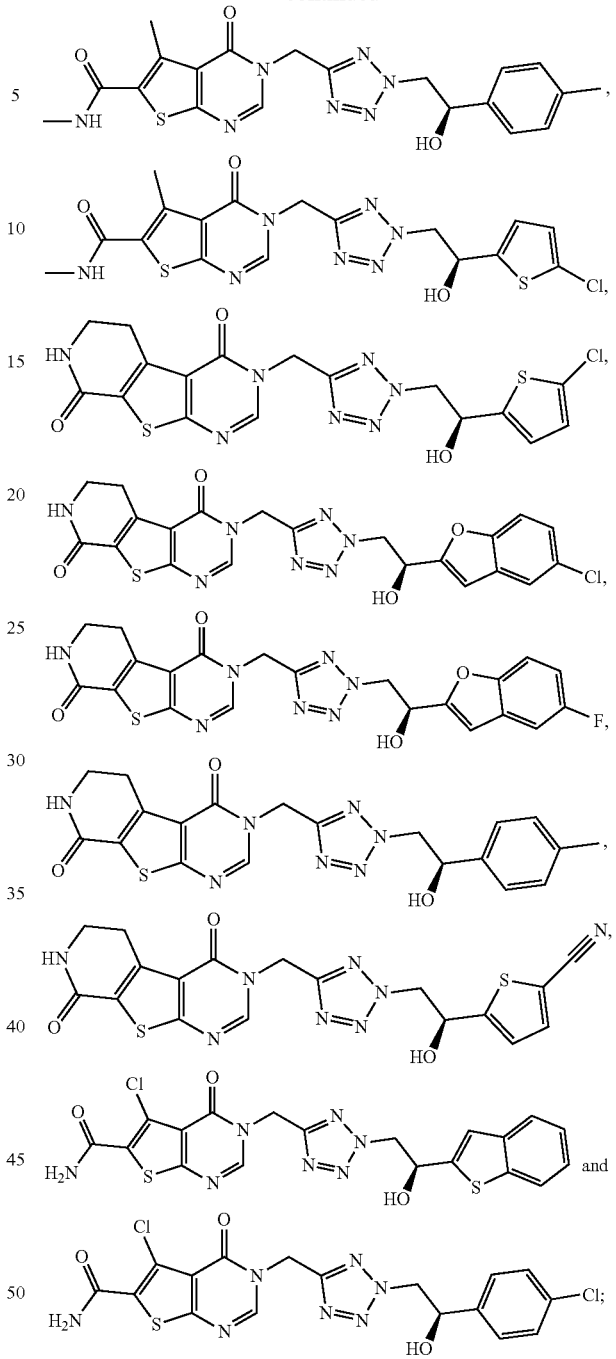

or pharmaceutically acceptable salt thereof.

10. A pharmaceutically acceptable salt of a compound according to claim 1.

11. A pharmaceutical composition comprising at least one compound of formula I according to claim 1, or a pharmaceutically acceptable salt thereof, and one or more pharmaceutically acceptable excipients.

12. A method for treating or preventing an inflammatory airway disease, a fibrotic disease or cough comprising administering to a patient having such disease or cough an effective amount of a compound according to claim 1 or a pharmaceutically acceptable salt thereof.

13. A method according to claim 12, wherein the patient has idiopathic pulmonary fibrosis (IPF) or cough.

14. A compound having the following formula:

or a pharmaceutically acceptable salt thereof.

15. A compound having the following formula:

or a pharmaceutically acceptable salt thereof.

16. A compound having the following formula:

or a pharmaceutically acceptable salt thereof.

17. A compound having the following formula:

or a pharmaceutically acceptable salt thereof.

18. A compound having the following formula:

or a pharmaceutically acceptable salt thereof.

19. A compound having the following formula:

or a pharmaceutically acceptable salt thereof.

20. A compound having the following formula:

or a pharmaceutically acceptable salt thereof.

21. A compound having the following formula:

or a pharmaceutically acceptable salt thereof.

22. A compound having the following formula:

or a pharmaceutically acceptable salt thereof.

23. A compound having the following formula:

or a pharmaceutically acceptable salt thereof.

24. A compound having the following formula:

25. A compound having the following formula:

26. A compound having the following formula:
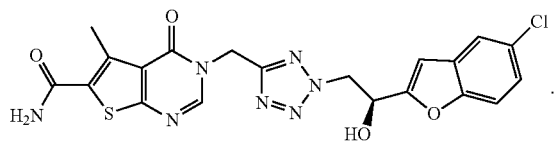 [SMILES: Cc1c(C(N)=O)sc2ncn(Cc3nnn(C[C@H](O)c4cc5cc(Cl)ccc5o4)n3)c(=O)c12]
27. A compound having the following formula:
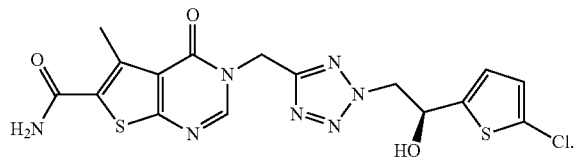 [SMILES: Cc1c(C(N)=O)sc2ncn(Cc3nnn(C[C@H](O)c4ccc(Cl)s4)n3)c(=O)c12]
28. A compound having the following formula:
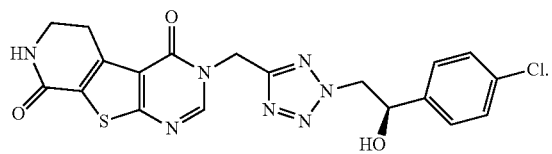 [SMILES: O=C1NCCc2c1sc1ncn(Cc3nnn(C[C@H](O)c4ccc(Cl)cc4)n3)c(=O)c21]
29. A compound having the following formula:
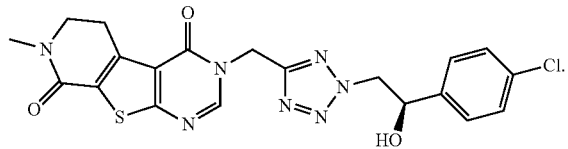 [SMILES: CN1CCc2c(sc3ncn(Cc4nnn(C[C@H](O)c5ccc(Cl)cc5)n4)c(=O)c23)C1=O]
30. A compound having the following formula:
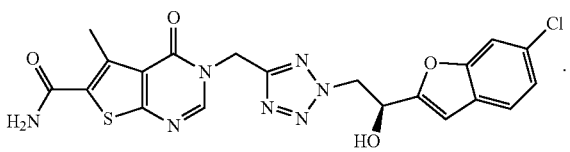 [SMILES: Cc1c(C(N)=O)sc2ncn(Cc3nnn(C[C@H](O)c4cc5ccc(Cl)cc5o4)n3)c(=O)c12]
31. A compound having the following formula:
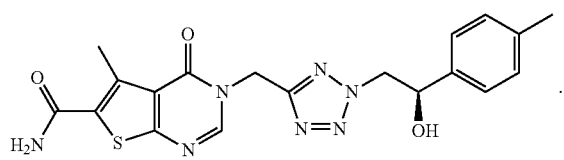 [SMILES: Cc1ccc([C@@H](O)Cn2nnc(Cn3cnc4sc(C(N)=O)c(C)c4c3=O)n2)cc1]
32. A compound having the following formula:
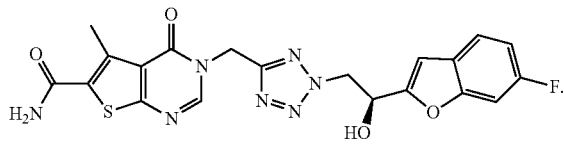 [SMILES: Cc1c(C(N)=O)sc2ncn(Cc3nnn(C[C@H](O)c4cc5ccc(F)cc5o4)n3)c(=O)c12]
33. A compound having the following formula:
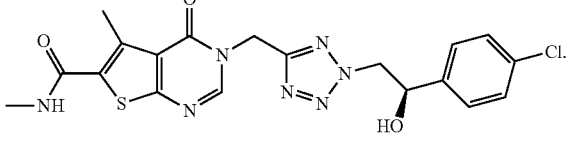
* * * * *